United States Patent
Riegel et al.

(10) Patent No.: US 7,282,576 B2
(45) Date of Patent: Oct. 16, 2007

(54) COACTIVATORS IN THE DIAGNOSIS AND TREATMENT OF BREAST CANCER

(75) Inventors: Anna T. Riegel, Washington, DC (US); Ronald Reiter, Sølzburg (AT); Anton Wellstein, Washington, DC (US)

(73) Assignee: Georgetown University, Washington, DC (US)

( * ) Notice: Subject to any disclaimer, the term of this patent is extended or adjusted under 35 U.S.C. 154(b) by 251 days.

(21) Appl. No.: 10/751,113

(22) Filed: Jan. 5, 2004

(65) Prior Publication Data

US 2004/0259114 A1 Dec. 23, 2004

Related U.S. Application Data

(63) Continuation of application No. PCT/US02/21066, filed on Jul. 3, 2002, now abandoned.

(60) Provisional application No. 60/302,648, filed on Jul. 5, 2001.

(51) Int. Cl.
C07H 21/04 (2006.01)

(52) U.S. Cl. ............... 536/23.1; 536/23.5; 435/252.3; 435/320.1

(58) Field of Classification Search .............. 536/23.1
See application file for complete search history.

(56) References Cited

U.S. PATENT DOCUMENTS 6,562,589 B1 * 5/2003 Meltzer et al. .......... 435/69.1

OTHER PUBLICATIONS

Reiter et al (J of biological Chemistry, 2001, 276:39736-39741, IDS).*
Chen et al (Cell, 1997, 90:569-580).*
Takeshita et al (J of Biological Chemistry, 1997, 272:27629-27634).*
Information Hyperlinked over Proteins (iHOP), p. 1-6.*
Tuschi, Thomas, "RNA Interference and Small Interfering RNAs," *Chembiochem*, 2(4): 239-245 (2001).
Wang, Zhlyong et al., "Regulation of Somatic Growth by the p160 Coactive p/CIP," *PNAS*, 97(25): 13549-13554 (2000).
Reiter, Ronald et al., "An Isoform of the Coactivator AIB1 That Increases Hormone and Growth Factor Sensitivity is Overexpressed in Breast Cancer," *Journal of Biological Chemistry*, 276(43):39736-39741 (2001).

* cited by examiner

*Primary Examiner*—Shanon Foley
*Assistant Examiner*—Laura B Goddard
(74) *Attorney, Agent, or Firm*—Morrison & Foerster LLP

(57) ABSTRACT

This invention relates to the AIB1 protein as a coactivator that potentiates the transcriptional activity of nuclear hormone receptors. The gene is amplified in a subset of human breast cancers. One splice variant of AIB1 transcribes a mRNA that lacks the exon 3 sequence. Δ3-AIB1 mRNA encodes a 130 kDa protein that lacks the N-terminal basic helix-loop-helix and a portion of the PAS dimerization domain. This 130 kDa protein was detected in MCF-7 breast cancer cells at levels 5-10% of the full length protein, whereas in non transformed mammary epithelium lines the Δ3-AIB1 protein is present at significantly lower levels compared to the full length AIB1. The abundance of Δ3-AIB1 mRNA is increased in human breast cancer specimens relative to that in normal breast tissue. Functional reporter gene assays revealed that the ability of Δ3-AIB1 to promote transcription mediated by the estrogen or progesterone receptors was significantly greater than that of the full-length protein. The Δ3-AIB1 isoform was also more effective than AIB1 in promoting transcription induced by epidermal growth factor. Thus, over expression of Δ3-AIB1 plays an important role in sensitizing breast tumor cells to hormone or growth factor stimulation.

3 Claims, 9 Drawing Sheets a b c a b a b a b

SEQUENCE LISTING

<160> NUMBER OF SEQ ID NOS: 3

<210> SEQ ID NO 1
<211> LENGTH: 35

-continued

```
<212> TYPE: DNA
<213> ORGANISM: Homo sapiens

<400> SEQUENCE: 1
tgccatgtga tactccagga caaggtctta cctgc                               35

<210> SEQ ID NO 2
<211> LENGTH: 34
<212> TYPE: DNA
<213> ORGANISM: Homo sapiens

<400> SEQUENCE: 2
aagagcaagg aaaaactatt tccaatgatg atga                                34

<210> SEQ ID NO 3
<211> LENGTH: 50
<212> TYPE: DNA
<213> ORGANISM: Homo sapiens

<400> SEQUENCE: 3
tgccatgtga tactccagga caagggaaaa actatttcca atgatgatga               50
```

COACTIVATORS IN THE DIAGNOSIS AND TREATMENT OF BREAST CANCER

REFERENCE TO RELATED APPLICATIONS

This application is a continuation of PCT/US02/21066 with an international filing date of Jul. 3, 2002, now abandoned, which claims the benefit of priority to U.S. Provisional Application No. 60/302,648, entitled "Coactivators in the Diagnosis and Treatment of Breast Cancer," filed Jul. 5, 2001. The entireties of both applications are hereby incorporated by reference.

STATEMENT REGARDING FEDERALLY SPONSORED RESEARCH OR DEVELOPMENT

Work described herein was funded, in whole or in part, by the USAMRC Breast Cancer Research Program Grant #BC980584. Department of Defense Grant #DAMD17-99-1-9203, and NIH Grant #P50 CA58185. The United States government has certain rights in this invention.

BACKGROUND OF THE INVENTION

1. Field of the Invention

The present invention relates to coactivators of hormone and growth factor activity in cancer cells and, specifically, to isoforms of the coactivator amplified in breast. In particular, the invention relates to compositions, diagnostic kits and methods for utilizing coactivator isoforms for the diagnosis, treatment and prevention of cancers such as breast cancer.

2. Description of the Background

Ligands such as estrogen and progesterone that interact with nuclear receptors regulate gene expression predominantly at the transcriptional level. The ligand-bound receptors interact specifically with DNA and activate transcription by recruiting a preinitiation complex. Although such gene activation was originally thought to be mediated by interaction of the receptors with components of the basal transcriptional machinery (1-6), a variety of screening techniques has identified a family of receptor-interacting proteins known as nuclear receptor coactivators (7-11). A common characteristic of this superfamily of proteins is that, when overexpressed in the presence of nuclear receptors, they potentiate ligand induction of transcription (12, 13). The related p160 group of coactivators, which include steroid receptor coactivators (Src-1), Src-2, and Src-3 (which is also known as AIB1, ACTR, RAC3, TRAM-1, and p/CIP) (14-20), possess several similar structural features including a receptor interaction domain (RID), a bHLH (basic helix-loop-helix)PAS (Per-Arnt-Sim homology) dimerization domain, and a CBP interaction domain (CID) (13). Coactivators are thought to function as bridges between nuclear receptors and either other coactivators or the basal transcriptional machinery (13). It was discovered that coactivators possess a histone acetylase domain (15, 21-24), which suggests that these proteins also might serve to regulate chromatin structure.

A portion of human chromosome 20 q that is frequently amplified in breast cancer contains the gene for the nuclear coactivator AIB1 (amplified in breast cancer 1) (25). The AIB1 gene is amplified in five to ten percent of breast cancers and the abundance of the corresponding mRNA and protein is increased in 30-50% of breast tumors and also breast cancer cell lines (14, 25-27). It has recently been shown that AIB1 binds directly to ER (28) and that AIB1 is rate-limiting for estrogen-induced growth of MCF-7 cells (29). However, the overall role of AIB1 for breast tumorigenesis has not been clear since AIB1 potentiates not only the action of estrogen (14, 16) and progesterone (16) receptors, but also that of various other nuclear receptors (9, 15, 17-20) and transcription factors (30, 31). In addition, several splice variants of SRC family members have been described, although the functions of these variants remain unknown (13).

SUMMARY OF THE INVENTION

The present invention overcomes the problems and disadvantages associated with current strategies and designs and provides new isoforms of the coactivator AIB1 including compositions, diagnostic kits, and treatments utilizing and derived from these isoforms. Further, the invention also provides novel siRNA molecules directed to these isoforms and methods for the treatment and prevention of cancer.

The invention relates to the identification and isolation of isoforms of the transcriptional coactivator, AIB1 protein. Isoforms include, but are not limited to, deletion mutants, addition mutants, and splice variants of the wild-type protein. Isoforms can be identified, for example, by an altered molecular weight or by an altered level of expression, which may be over expression or under expression, in breast cancer tissue and other tissues and cell lines. One splice variant is Δ3-AIB1, whose transcript encodes a N-terminal truncated version of AIB1 that lacks the HLH and PAS A domain and has a molecular weight of 130 KDa. In functional studies, it has been determined that the Δ3-AIB1 protein is a significantly more effective coactivator of estrogen, progesterone and EGF signaling as compared to the wild type ER, providing a role for this AIB1 isoform in hormone and paracrine signaling in breast cancer.

One embodiment of the invention is directed to isoforms of the AIB1 transcriptional coactivator protein. Isoforms are potent transcriptional coactivators of nuclear receptors (e.g. retinoid, steroid such as estrogen receptor or progesterone receptor, thyroid), and/or potentiate growth factor activities such as signaling pathways. Transcriptional coactivators function by enhancing transcription induced by a transcription factor. Enhancement is thought to be produced by binding to a transcription factor which forms a complex that promotes transcription of a gene, and not by direct binding of the coactivator to a site on the respective genome. Preferably, coactivation by an isoform is significantly greater than coactivation produced by wild-type AIB1 protein. Preferably, the isoform contains a deletion of all or significant portions of exon 3 in the amino terminus of the protein (exon 3 encompasses NT positions 266-438 as counted from a transcription start site), and is over expressed in cancer cells such as, for example, breast tumor tissue and prostate tumor tissue. Although there may exist alternate transcription start sites, exon 3 is the first exon 3' of the exon containing a translation start site.

Another embodiment of the invention is directed to isolated nucleic sequences that encode isoforms of the invention. Preferably the nucleic acid encodes the isoform Δ3-AIB1. The invention further encompasses vectors that contains the nucleic acid of isoforms of the invention, and also recombinant cells, which may be either eukaryotic or prokaryotic, containing nucleic acids or vectors of the invention.

Another embodiment of the invention is directed to diagnostic kits for the detection of cancer comprising chemical substances that are specifically reactive and preferably bind to AIB1 and isoforms of the invention. The diagnostic kits preferably contain antibodies or antibody fragments directed against AIB1 and/or isoform proteins of the invention, or identifiable fragments of these proteins that are distinguishable. Antibodies may be monoclonal or polyclonal, or antibody fragments which may comprise recombinant or humanized proteins. The invention further relates to antibodies or antibody fragments that are specifically reactive to the isoform of the invention. Preferably such antibodies or antibody fragments are IgG isotypes.

Another embodiment of the invention is directed to methods for the detection of cancer in a patient comprising contacting a biological sample obtained from the patient to one or more chemical substances that specifically bind to AIB1 and/or isoform of the invention (either the protein or RNA product of transcription), and detecting binding of one or more of the chemical substances. Chemical substances are preferably antibodies specific to the coactivator proteins or nucleic acids that are complementary to their genetic sequences. The method may further comprise comparing the relative amount of isoform in the sample with the amount of wild-type AIB1 protein in the sample, for example, to determine a stage of the cancer such as a hormone-independent phenotype.

Another embodiment of the invention is directed to pharmaceutical compositions comprising an agent that specifically binds to the isoform of the invention and prevents a coactivation function when administered to a patient. Preferably compositions contain a pharmaceutically acceptable carrier such as, for example, alcohols, buffers, fatty acids, glycerol, oils, polysaccharides, saccharides, salts, sugars, water, and combinations thereof.

Another embodiment of the invention is directed to small interfering RNA molecules (siRNA) that inhibit expression of a transcriptional coactivator protein such as, for example, AIB1, isoforms of AIB1 such as the p160 group of coactivators, Src-1, Src-2, Src-3, and other isoforms, fragments and combinations thereof. Preferably, the siRNA is specifically targeted to inhibiting the expression of one protein isoform and does not target other isoforms. One preferred siRNA targets the Δ3-AIB1 mRNA and contains sequences homologous and complementary to that mRNA. Preferably the siRNA contains a sequence, a portion of which is derived from exon 2 of the mRNA that encodes Δ3-AIB1, and another portion of which is derived from exon 4 of the mRNA that encodes Δ3-AIB1. The portions are each preferably from about 5 to about 16 nucleotides in length, making the total length of the RNA molecule about 12 to about 32 nucleotides long. That sequence together with sequence complementary thereto, forms the double-stranded siRNA molecule.

Another embodiment of the invention is directed to pharmaceutical compositions comprising siRNA that inhibits expression of transcriptional coactivator proteins and a pharmaceutically acceptable carrier. Preferably pharmaceutically acceptable carriers include alcohols, buffers, fatty acids, glycerol, oils, polysaccharides, saccharides, salts, sugars, water, and combinations thereof. Pharmaceutical composition of the invention may further include one or more anti-neoplastic agents effective in the treatment of cancer such as, for example, agents that inhibit cell growth, agents that inhibit cell proliferation, agents that inhibit cellular differentiation, anti-angiogenic agents, antibodies, antibody fragments, anti-sense agents, chemical agents, cytokines, toxins, and combinations thereof.

Another embodiment of the invention is directed to methods for treating or preventing a tumor comprising administering to a patient a therapeutically effective dose of a pharmaceutical composition of the invention. Administration is preferably by direct injection to the tumor. These method may further comprise administering additional tumorigenic therapy to the patient such as, for example, drug therapy, radiation therapy, surgery, and combinations thereof.

Another embodiment of the invention is directed to transgenic animals and methods for the creation of transgenic animals containing nucleic acid sequences that express AIB1 and/or isoforms, or siRNA directed against AIB1 or isoforms of the invention. Preferably the animal is a mouse and the isoform is Δ3-AIB1.

Other embodiments and advantages of the invention are set forth in part in the description which follows, and in part, will be obvious from this description, or may be learned from the practice of the invention.

DESCRIPTION OF THE FIGURES

FIG. 3 Comparison of the abundance of Δ3-AIB1 mRNA between malignant and nonmalignant human breast tissue and cell lines showing: a total RNA isolated from MCF-7, MCF-10A, and A1N4 cells subjected to Southern blot analysis with a probe specific for exon 4 of AIB1; b total RNA isolated from six normal breast and eight breast cancer tissue samples analyzed as in a.

DESCRIPTION OF THE INVENTION

Figure 1:
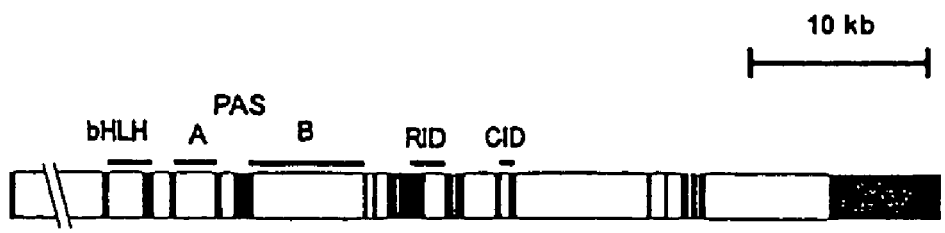
FIG. 1 Characterization of a splice variant of human AIB1 showing: a the structure of human AIB1; b the positions of PCR products corresponding to the full-length (AIB1) and truncated (Δ3-AIB1) transcripts; and c the positions of the splice junctions in Δ3-AIB1 mRNA and of the encoded protein domains.
Figure 1:
Figure 1:
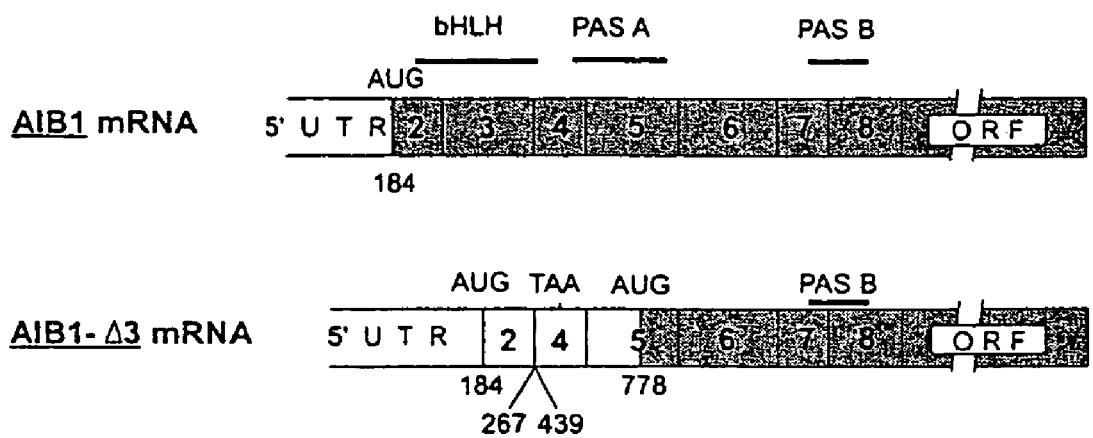

As embodied and broadly described herein, the present invention is directed to novel isoforms of the coactivator AIB1. In particular, the invention relates to compositions containing these isoforms and pharmaceutical compounds that relate to their method of action, to diagnostic kits for detecting such isoforms in cells, to methods for utilizing the compositions and kits, and to methods for the prevention and treatment of cancer including, but not limited to, breast cancer.

A portion of human chromosome 20 q that is frequently amplified in breast cancer contains the gene for the nuclear receptor coactivator AIB1 (amplified in breast cancer 1) (25). Nuclear receptors include, but are not limited to, bile acid receptors, perxoidone proliferator receptors, retinoid receptors, steroid receptors such as, for example, estrogen receptors and progesterone receptors, thyroid receptors, vitamin D receptors and others, which regulate gene expression predominantly at the transcriptional level. Coactivators are proteins whose expression enhances transcriptional activation of nuclear regulators, i.e. molecules that regulate gene expression. These coactivators are thought to function by binding to transcription factors and forming a complex that enhances induced transcription, and not by binding directly to the genome. The AIB1 gene is amplified in five to ten percent of breast cancers and the abundance of the corresponding mRNA and protein is increased in some breast tumors and breast cancer cell lines (14, 25-27). It has recently been shown that AIB1 binds directly to ER (28) and that AIB1 is rate-limiting for estrogen-induced growth of MCF-7 cells (29). However, the overall role of AIB1 for breast tumorigenesis is not clear since AIB1 potentiates not only the action of estrogen (14, 16) and progesterone (16) receptors, but also that of various other nuclear receptors (9, 15, 17-20) and transcription factors (30, 31). Isoforms of AIB1 are closely-related polypeptides derived from the same gene and functionally similar. Isoforms include, but are not limited to, polypeptides translated from different transcription and/or translation start sites, frame-shift mutations, and splice variants of the mRNA that exist as functional proteins. Several splice variants of Src family members have been described in vitro, although their existence in vivo is not known and the functions of these cDNA, if any, remain unknown, none were translated into protein (13).

It was surprisingly discovered that an isomer of AIB1, a splice variant of AIB1 that has exon 3 deleted, the Δ3-AIB1 mRNA, is translated in vivo in breast cancer cells into an $NH_2$-terminal truncated form of AIB1. This N-terminally truncated version of AIB1 has lost most of the predicted dimerization domains and thus is more promiscuous with respect to potential interaction partners (48). The predicted size of this truncated protein is approximately 130 kDA and a protein with this molecular weight was identified in Western blot analysis of MCF-7 cells (48). In support of the significance of the N-terminal region, it was found that over expression of the Δ3-AIB1 isoform potentiates nuclear hormone (ER, PR) and growth factor (EGF) induction of transcription to a much greater extent than full-length AIB1 (48). This indicates that over expression of this isoform in cancer plays a role in sensitizing breast cancer cells to hormone and/or growth factor induced changes in phenotype during the malignant progression of breast cancer.

Δ3-AIB1 has several unusual properties of interest. First, on a per molecule basis, Δ3-AIB1 is a potent transcriptional coactivator of steroid receptors such as, for example, the estrogen receptor and the progesterone receptor (see e.g. Example 4), and also growth factor signaling (e.g. see Example 5). It is also a more potent coactivator than full-length AIB1 protein as measured by conventional transcriptional assays such as, for example, a transient transfection assay (see e.g. Example 4). For a given amount of vector transfected, the amount of Δ3-AIB1 protein produced in transient assays is only about 1% to 10% that of the full-length protein (48). Despite this, the coactivating effect of Δ3-AIB1 is several-fold greater than full-length AIB1 making it highly effective on a molar basis. This result is unexpected given that previous studies of $NH_2$-terminal deletion mutants of the AIB1-related protein Src-1 did not reveal an impact of this region on nuclear receptor signaling (9, 30). One reason for the increased activity of Δ3-AIB1 is that the conformation of this isoform is more favorable than that of the full-length protein for interaction with nuclear receptors or for recruitment of other coactivators such as CBP/p300. Another reason is indicated by the observation that the bHLH-PAS domains of Src-1 interacts with and potentiates the activity of members of the TEF family of transcription factors (30). Thus, full-length AIB1 is unavailable for interaction with nuclear receptors because it is sequestered or squelched by other intracellular factors. In contrast, AIB1-Δ3, which lacks an intact bHLH-PAS domain, would not bind to potential repressors such as TEF and would be available for nuclear receptor coactivation. This may explain why relatively small amounts of recombinant Δ3-AIB1 are able to induce significant potentiation of nuclear receptor activity in transfected COS-1 cells with a high background of endogenous full-length AIB1. This model also predicts that the relative coactivating effects of AIB1 and Δ3-AIB1 are likely cell-type specific, depending on the endogenous expression of AIB1-sequestering molecules such as TEF. A recent report described that the human MMS19 protein can interact with the PAS-HLH domain of AIB1 and can regulate ER-mediated transcriptional activity (43). The lack of interaction of Δ3-AIB1 with this protein explains some of its increased effectiveness in vivo. The data indicates that expression of the AIB1 isoform sensitizes cells to the effects of estrogen and progesterone.

The second aspect of the function of the Δ3-AIB1 isoform is that it also increases EGF signaling in ME-180 squamous carcinoma cells. This may be through direct interactions with a nuclear receptor. However, analysis of the fragment of the FGF-BP gene promoter (nt −118 to +62, relative to the transcription start site) used in this study did not reveal obvious consensus recognition sites for known nuclear receptors. In fact, EGF induction of this promoter is dependent on the factors AP-1 and c/EBPβ (32), either of which may interact directly or indirectly with AIB1. Alternatively it may be that a common intermediary of both nuclear receptor and AP-1 signaling such as CBP/p300 (44, 45) may be the target of the superactivating effects of the Δ3-AIB1 isoform. Whatever the mechanism of the increased potentiation of growth factor signaling by the Δ3-AIB1 isoform, the data suggest that an increase in the abundance of the Δ3-AIB1 isoform in mammary epithelial cells may be an important step in tumor progression and to the development of a more aggressive, hormone-independent phenotype.

Of major interest for breast cancer is that the Δ3-AIB1 mRNA is over expressed in breast cancer cell lines and in human breast and ovarian tumors. While the increase in expression in tumors may be due, in part, to dilution effects of surrounding stromal tissue, this seems unlikely given the lower Δ3-AIB1 mRNA expression in non transformed versus malignant mammary epithelial cell lines. To date, a number of laboratories, have reported overexpression of AIB1 mRNA and protein in breast tumor tissue although the assessment of the portion of breast cancers overexpressing AIB1 varies widely between groups (14, 27, 46, 47). In addition, some groups have determined that AIB1 overexpression is correlated with ER and PR status (26) while others have found an inverse relationship with steroid receptor expression, but a positive correlation with HER-2 and p53 expression (47). However, all of these RT-PCR or immunohistochemical analyses of expression levels have not distinguished the Δ3-AIB1 isoform signal from that of the wild type. The data indicates that overexpression of relatively low levels of the Δ3-AIB1 isoform can sensitize cells to estrogen, progesterone and growth factors. Therefore, measurement of increased levels of Δ3-AIB1 levels is likely a sensitive indicator of the progression of breast cancer to a more hormone-independent phenotype.

Using ribozyme targeting that down regulates AIB1, it was determined that down regulation leads to loss of estrogen reduction and proliferation of breast cancer cells in vivo. To analyze over expression of Δ3-AIB1 in transgenic animals, a transgenic animal was made that expressed the Δ3-AIB1 protein under CMV control. The phenotype observed in these animals is that at about 7 weeks old, the male mice develop large mammary glands. Upon whole mount examination of these mice, it was determined that the mammary glands contain massive stromal proliferation leading to large fat tissue in the breast. Thus, the effect of the Δ3-AIB1 isoform is to increase proliferation of stromal cells and/or increase the differentiation of fibroblasts to adipocytes. This same phenotype is seen in the female, although not as pronounced, but the stromal tissue is already quite large at seven weeks and also in other fat tissue and the stroma of the female. This indicates that the Δ3-AIB1 isoform can play a role in aberrant expression or proliferation of stroma in breast cancer and other endocrinological malignancies and pathologies. Since a previously made AIB1 knockout mouse has been shown to be a small animal with defects in IGF signaling, the defect from the over expression of Δ3-AIB1 is likely from over expression of IGF1 in the liver as can be determined by measuring IGF1 in the serum. These animals will likely develop a fat phenotype later in life indicating that Δ3-AIB1 and AIB1 have a wider role in fat metabolism. Its also possible that the effect of Δ3-AIB1 is not mediated through IGF1, but through the PPAR system (perxoidone proliferator receptor), which is known to be central to fat metabolism.

Accordingly, one embodiment of the invention is directed to protein isoforms of the AIB1 coactivator. Preferably these isoforms are potent transcriptional coactivators of nuclear receptors including, but not limited to, retinoid receptors, steroid receptors such as estrogen and progesterone, thyroid receptors, and vitamin D receptors. Further, it is also preferred that these isoforms potentiate growth factor signaling pathways such as signaling through, for example, EGF, FGF, and PTN, and preferably significantly or measurably more so than the wild-type AIB1 protein. Isoforms of the invention include proteins that contain deletions, additions or mutations (e.g. point, frame shift). Isoform deletions include, but are not limited to, deletions of a portion of the C terminus, a portion of the N-terminus, the bHLH domain, the PAS A domain, the PAS B domain, RID, CID, exons 1, 2, 3, 4, 5, 6, 7, 8, 9, the intervening introns, and/or portions or combinations thereof. Preferably, the isoform contains a deletion of exon 3 in the amino terminus of the protein. Also preferably, the isoform is over expressed or under expressed in cancer cells including, but not limited to cancers of the breast, gastric cancers, head and neck cancers, ovarian cancer, pancreatic cancer, prostate cancer, squamous cell cancers, and tumors, as well as other epithelial cell cancers, or combinations thereof, and thereby can be used to detect and identify such cancerous conditions and metastasis related thereto both in vivo and in biological samples in vitro.

Another embodiment of the invention is directed to isolated nucleic acid sequences that encode one or more isoforms of the invention. Preferably the nucleic acid, which may be DNA, RNA or PNA, encodes the isoform Δ3-AIB1 containing a deletion of exon 3 from about positions 267 to 439. Please note, currently there is no accepted exon numbering. The numbering for the exons herein is based on the experiments set forth in the examples section and cited publications. However, based on the information provided herein such as specific sequence information of the AIB1 gene (FIG. 9), the locations of the binding sites along AIB1 (FIG. 1 and FIG. 9), and the transcription and translation start sites (FIG. 1 and FIG. 9), any different exon numbering system can be readily and easily correlated to those disclosed herein by those of ordinary skill in the art. The invention further encompasses vectors (e.g. plasmids, cosmids, viral, or shuttle vectors) that contains the nucleic acid of isoforms of the invention, and also recombinant cells, which may be either eukaryotic or prokaryotic (e.g. Enterobacter, *Escherichia coli*, or *Bacillus subtilis*), containing nucleic acids or vectors of the invention.

Another embodiment of the invention is directed to diagnostic kits for the detection of cancer comprising chemical substances that are specifically reactive to one or more protein isoforms of the invention, or nucleic sequences that encode these isoforms. Such chemical substances include, for example, aptamers, antibodies, ligands, nucleic acids (e.g. that are complementary to genes or mRNA), protein binding partners (e.g. ligands), and fragments and combinations thereof. The diagnostic kits preferably contain antibodies or antibody fragments, such as, for example, monoclonal or polyclonal antibodies, or antibody fragments which may be recombinant or humanized proteins, directed against a particular isoform or portion of an isoform. Antibodies may be covalently or non-covalently labeled with one or more report molecules, such as, for example, a fluorescent label, for detection and identification. By selecting only portions of isoforms, those with specific regions (e.g. binding domains, exons, etc.), can be identified and if desired selected. Further, identification and selection can be used to determine the relative amounts of protein or nucleic acid molecules in a sample in vitro, or in vivo. Samples may be almost any biological sample obtained from a patient, such as a human, including but not limited to blood, biological fluids, cells, plasma, and most any other tissues. Preferably such antibodies or antibody fragments are IgG isotypes, but may be IgA, IgD, IdE or IgM, or fragments (e.g. Fv fragments) or combinations thereof. The types of cancer that can be detected, identified and possibly therapeutically and/or prophylactically treated include, but are not limited to breast cancers, bone cancers, endothelial cancers, epithelial cancers, gastrointestinal cancers, head and neck cancers, ovarian cancers, metastatic cancers, neuroblastomas, pancreatic cancers, prostate cancers, squamous cell cancers, stomach cancers, and tissue-specific as well as non-tissue specific tumors. This basically include most any disorder that demonstrates either increased or decreased expression of AIB1 or an AIB1 isoform.

Another embodiment of the invention is directed to methods for the detection of a cancer in a patient comprising contacting a biological sample obtained from the patient to one or more chemical substances that specifically bind to protein isoforms of the invention (or their genetic sequences), and detecting binding of one or more of the chemical substances thereto. The patient may be a human or other primate, or another mammal, Samples may be liquid or solid, such as blood, cells, plasma, tissues or other biological materials, but are preferably tissue samples of the area suspected to contain a cancerous region. The method may further comprise comparing the relative amount of isoform in the sample (e.g. protein or mRNA) with the amount of wild-type AIB1 (e.g. protein or mRNA), or the amounts of one isoform or fragment in comparison to others. This can help to determine a stage of the cancer as being more or less aggressive, a phenotype such as a hormone-independent phenotype, a relative resistance or sensitivity to conventional treatment, or the amount of steroid or growth factor being sequestered by one or more isoforms for detection or treatment purposes.

Another embodiment of the invention is directed to pharmaceutical compositions comprising an agent that specifically binds to the isoform of the invention and prevents a coactivation function when administered to a patient. Preferably compositions contain one or more pharmaceutically acceptable carriers such as, for example, alcohols, buffers, fatty acids, glycerol, oils, polysaccharides, saccharides, salts, sugars, water, and combinations thereof.

Another embodiment of the invention is directed to small interfering RNA (siRNA) molecules directed against mRNA that encode transcriptional coactivator proteins. These siRNA molecules are double-stranded and typically between about 10 bp and 50 bp in length, preferably between about 15 bp and 30 bp, and more preferably between about 18 bp and 25 bp. Methods for manufacturing such RNA molecules with any desired sequence have been previously described (see U.S. Pat. No. 5,795,715), as has their use in controlling gene expression (see 51 and 55-65). These molecules are directed against transcriptional coactivators and, preferably, the transcriptional coactivator proteins AIB1, Src-1, Src-2, Src-3, and related isoforms such as, for example, Δ3-AIB1. The siRNA molecule directed against the Δ3-AIB1 mRNA contains sequences that are homologous and complementary to a mRNA that encodes Δ3-AIB1, and that hybridize to each other to form the double-stranded RNA molecule. Preferably, siRNA molecules contains sequences derived from each side of the region that is deleted such that only the particular isoform mRNA is targeted. For example, a preferred siRNA contain a sequence from a portion of exon 2 of the mRNA that encodes Δ3-AIB1, and another portion of which is derived from exon 4 of the mRNA that encodes Δ3-AIB1. Another preferred anti-AIB1 siRNA for identifying isoforms containing a deletion of the PAS A binding site contains a sequence wherein a portion is derived from the sequence on one side of the PAS A binding site and another portion is derived from a sequence on the other side of the PAS A binding site. Preferably the portions are similar in length to provide good interaction across the deletion and contiguous in the resulting mRNA, but may be non-contiguous containing 1, 2, 3, 4, 5, 6, or more nucleotides between the portions. Alternatively, siRNAs may contain sequences that represent additions or new sequences of the isoform mRNA not found in the wild-type mRNA. Portions, and typically the corresponding sequences of the siRNA, are each preferably from about 4 to about 20 nucleotides in length, more preferably from about 6 to 16 nucleotides in length, and more preferably from about 8 to 12 nucleotides in length. Most preferably, the siRNA is capable of targeting one or a small number of isoforms of the particular coactivator, but not the wild-type coactivator mRNA. The greater the ability to distinguish an isoform from wild type, the greater the targeting ability to that isoform and the therapeutic benefit against disease that over expression or under expression of the isoform may cause. Further, the greater the ability to not interfere with wild type function, the less likely will be side effects and related complications of more general anti-coactivator therapy.

Another embodiment of the invention is directed to pharmaceutical compositions comprising siRNA that inhibits expression of one or more transcriptional coactivator proteins and, optionally, a pharmaceutically acceptable carrier. Preferably pharmaceutically acceptable carriers include alcohols, buffers, fatty acids, glycerol, oils, polysaccharides, saccharides, salts, sugars, water, and combinations thereof. Pharmaceutical composition of the invention may further include one or more anti-neoplastic agents effective in the treatment of cancer such as, for example, agents that inhibit cell growth, agents that inhibit cell proliferation, agents that inhibit cellular differentiation, anti-angiogenic agents, antibodies, antibody fragments, anti-sense agents, chemical agents, cytokines, toxins, and combinations thereof. Such combination treatments may be administered simultaneously or sequentially as may be determined from appropriate clinical trials.

Another embodiment of the invention is directed to methods for treating or preventing cancer (e.g. hard or soft tumor, leukemia, lymphoma) comprising administering to a patient a therapeutically effective dose of a pharmaceutical composition containing one or more types of siRNA molecules targeted to one or more form of AIB1 and/or AIB1 isoforms of the invention. Therapeutic and/or prophylactic benefit may be to treat or prevent a disease or simply to reduce side effects attributable to the activity of transcription factors (e.g. transcriptional enhancers such as TEF {transcription enhancing factor}, transcriptional repressors), ligand/receptor interactions (e.g. PTN {pleiotrophin}, RTK {receptor tyrosine kinase}), growth factors (e.g. EGF {epidermal}, FGF {fibroblast}, HGF {hepatocyte}, VEGF {vascular endothelial}, PDGF {platelet-derived}, IGF {insulin-like}), or tumor suppressor gene products (e.g. p53). As certain isoforms have a higher per molecule effectiveness, thus requiring lower amounts for therapeutic benefit, the dose response curve is significantly and positively shifted. This significantly lowers the risk of potentially harmful side effects, and provides a higher maximum effectiveness as compared to wild-type protein. Administration is preferably by direct injection to the site of the cancer such as the tumor, but may be systemic as determined empirically from clinical trials. Therapeutically effective doses can be determined by those of ordinary skill in the art and depend, in part, on the size of the patient or size of the area being treated and route of administration. Typically, systemic administration requires therapeutically effective doses that attain blood levels of from 2 nM to 2 mM, preferably about 2 μM. Localized administration may require that these same concentrations be achieved, but only in the localized areas of treatment (e.g. the tumor), and thus much lower overall amounts may be used. Treatments can be repeated often because the composition is non-toxic and/or non-carcinogenic, and safe for multiple and/or continued administration.

These method may further comprise administering additional anti-cancer, anti-metastatic, or anti-tumor therapy to the patient such as, for example, drug therapy, radiation therapy, surgery, and combinations thereof.

Another embodiment of the invention is directed to transgenic animals and methods for the creation of transgenic animals containing nucleic acid sequences that express isoforms of the invention or siRNA molecules directed against isoforms of the invention. Preferably the animal is a mouse, a primate or another mammal, and the isoform contains a deletion of one or more of the ligand binding domains such as ?3-AIB1. Transgenic animals can be used as models for drug testing and to determine the effectiveness of siRNA therapy.

The following examples illustrate embodiments of the invention, but should not be view as limiting the scope of the invention.

EXAMPLES

Example 1

Detection of the Δ3-AIB1 Isoform

In this study, it was first determined if there were naturally occurring splice variants of AIB1 present in breast cancer cells that might encode proteins with altered function relevant to breast cancer progression. All cell lines used were obtained from the tissue culture core facility of the Lombardi Cancer Center. MCF-7, ME-180, and COS-1 cells were cultured in Iscove's modified Eagle's medium (IMEM) (Life Technologies) supplemented with 10% fetal bovine serum (FBS). MCF-10A and A1N4 cells were grown in a 1:1 mixture of IMEM and Ham's F-12 medium (Life Technologies) that was supplemented with 5% horse serum, EGF (20 ng/ml), insulin (10 μg/ml), and hydrocortisone (500 ng/ml). CHO cells were maintained in F-12 Nutrient Mixture (Life Technologies) supplemented with 10% FBS.

Shown in FIG. 1 is a characterization of the splice variants of human AIB1. FIG. 1a shows the stricture of human AIB1 showing the 22 known exons (filled boxes) and the corresponding introns (open boxes). The exon/intron regions which are spliced to form the various functional domains of the AIB1 protein are indicated by horizontal bars. Shown in FIG. 1b is detection of the Δ3-AIB1 splice variant in total RNA from MCF-7 cells. Total RNA was subjected to RT-PCR with primers specific for exons 1 and 9 of AIB1. Reaction products were resolved on a 1% agarose gel and transferred to a PVDF membrane, which was then cut and the lanes were separately subjected to hybridization with $^{32}$P-labeled oligonucleotides specific for exons 2, 3, or 8 of AIB1. The positions of PCR products corresponding to the full-length (AIB1) and truncated (Δ3-AIB 1) transcripts are indicated. Shown in FIG. 1c is a comparison of the structures of AIB1 and Δ3-AIB1 mRNAs. The alternative splicing event that results in the loss of exon 3 causes the open reading frame (ORF) to shift and terminate at a TAA codon in exon 4. A potential initiation site (AUG) for Δ3-AIB1 mRNA is present at nt 778; the use of this site would be consistent with the Δ3-AIB1 protein lacking the NH$_2$-terminal 26 kDa of full-length AIB1. Shaded regions indicate the open reading frame, and exons in the mRNAs are numbered. The positions of the splice junctions in Δ3-AIB1 mRNA and of the encoded protein domains are indicated. UTR, untranslated region.

The exon-intron structure of AIB1 was assembled as shown in FIG. 1a by comparing the published sequence of the cDNA (14) with the contiguous genomic sequence available through the NCBI database. The most 5' exon of AIB1 was arbitrarily designated as exon 1, with the result that the first codon is located in exon 2. The initial strategy was to determine if RNA from MCF-7 cells ,which overexpress AIB1(14), contained any splice variant forms of AIB1 RNA. To achieve this, reverse transcription and polymerase chain reaction (RT-PCR) analysis was performed using total RNA from MCF-7 human breast cancer cells with primers amplifying the region between exons 1 and 9. Isolation of total RNA and synthesis of cDNA by RT were performed as described previously (33). Amplification of AIB1 cDNA sequences was achieved by PCR according to the following protocol: incubation at 95° C. for 5 min followed by 30 cycles of 95° C. for 1 min, 60° C. for 1 min, and 72° C. for 90 sec. Oligonucleotides used as primers for PCR or as probes for hybridization were for exon 1, exon 2, exon 3, exon 4, exon 5, exon 8, and exon 9. PCR products were separated by electrophoresis on a 1% agarose gel, transferred to a polyvinylidene difluoride membrane, and hybridized with a $^{32}$P-labeled oligonucleotide probe. Quantification of PCR products was performed with a Phosphorimager (Molecular Dynamics 445SI).

This revealed two PCR products that differed in size by ~150 bp. These PCR products were then subjected to Southern Blot analysis and individual lanes from the membrane were probed separately with oligonucleotides specific for each exon from 2 to 8. Typical hybridizations with exons 2, 3 and 8 are shown in FIG. 1b. This analysis revealed that the smaller PCR product hybridized with all probes except that specific for exon 3 (FIG. 1b), indicating that the lower band corresponds to an RNA splice variant (designated Δ3-AIB1) of AIB1 that lacks the exon 3 sequence. The PCR product was subsequently subcloned and sequenced, confirming that nucleotides (nt) 267 to 439 (exon 3) of the full-length AIB1 cDNA were missing (FIG. 1c).

The full-length AIB1 cDNA was subcloned from pCMX-ACTR into pcDNA3 (Invitrogen) with the use of the flanking KpnI and XhoI sites, thereby creating the expression vector pcDNA3-AIB1. The smaller of the two RT-PCR products generated from MCF-7 cell total RNA with exon 1- and exon 9-specific primers (FIG. 1b) was subdloned into pCRII (Invitrogen). The resulting plasmid was digested with BamHI and HpaI, recognition sequences which flank the splice sites of AIB1-Δ3 cDNA, and the released fragment was purified and used to replace the corresponding sequence of pcDNA3-AIB1, thereby creating pcDNA3-AIB1-Δ3. The pcDNA3-AIB1 and pcDNA3-AIB1-Δ3 vectors contain identical 5' and 3' untranslated regions, differing only in the loss of exon 3 in the latter. Inserts were verified by sequencing.

Example 2

Translation of the Δ3-AIB1 mRNA in Vitro and in Vivo

To determine if an AIB1 related protein was encoded by the Δ3-AIB1 mRNA, in vitro transcription and translation of Δ3-AIB1 cDNA was performed with the TnT coupled reticulocytelysate system (Promega). Plasmid DNA (1 μg) was combined with 25 μl of rabbit reticulocyte lysate, 2 μl of TnT reaction buffer, 1 μl of T7 RNA polymerase, 1 μl of amino acid mixture, 1 μl of Rnasin ribonuclease inhibitor (40 U), and 1 μl of Transcend biotin-lysyl-tRNA, and the final volume was adjusted to 50 μl. The reaction was performed at 30° C. for 90 min, after which 5 μl of the reaction mixture were subjected to SDS-polyacrylamide gel electrophoresis and either to immunoblot analysis with antibodies to AIB1 or to direct detection with streptavidin-conjugated horseradish peroxidase (1:10,000 dilution in phosphate-buffered saline containing 0.05% Tween-20) and enhanced chemiluminescence.

Figure 2:
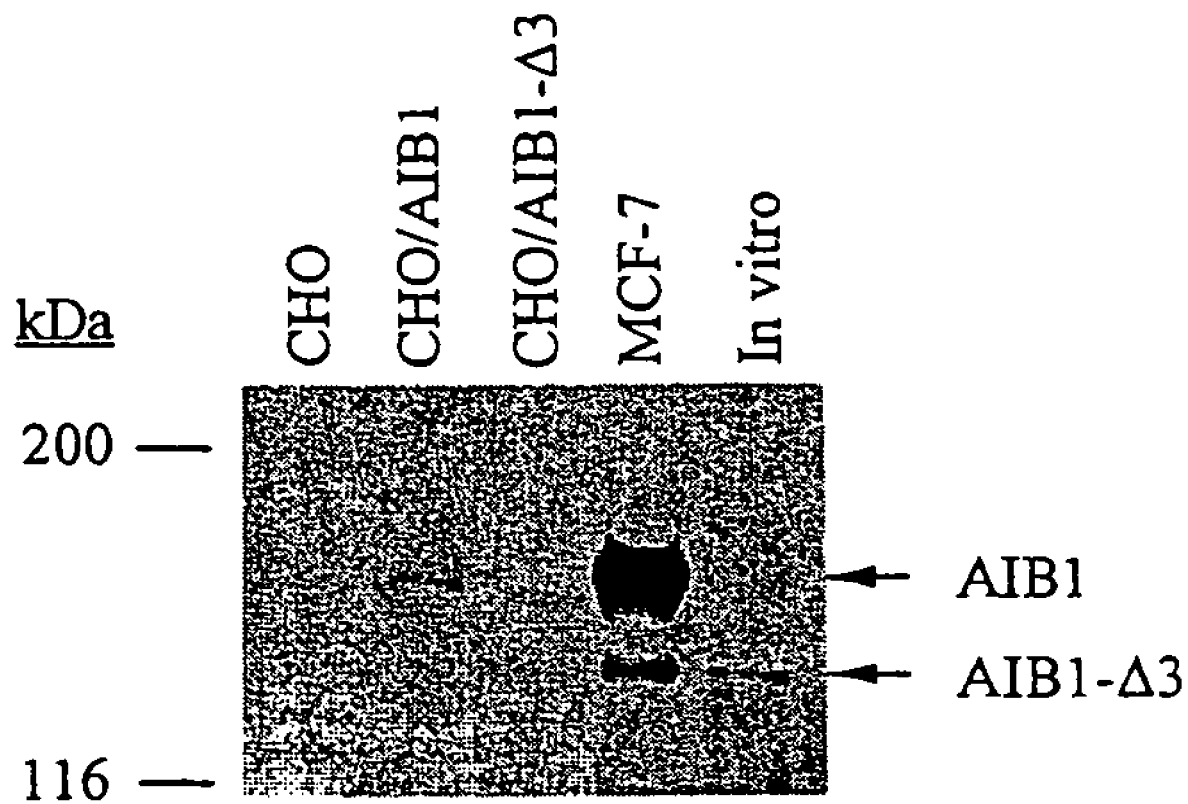
FIG. 2 Immunoblot analysis of AIB1 isoforms in extracts of MCF-7 cells and transfected CHO cells.

Western blot analysis with an AIB1 specific antibody of the proteins translated in vitro revealed the production of a 130-kDa protein (FIG. 2). Interestingly, a similar 130-kDa protein, in addition to the 156-kDa full-length AIB 1, was consistently detected by immunoblot analysis of MCF-7 cell extracts with antibodies to AIB1 on 5-20% polyacrylamide gels (27).

Whole cell extracts were prepared as described previously (32), and equal portions (30 μg of protein) were resolved either on denaturing 4-20% polyacrylamide gradient gels or on 4% polyacrylamide gels containing Tris-glycine. Separated proteins were transferred to a nitrocellulose membrane and then subjected to immunoblot analysis with a 1:500 dilution of a mouse monoclonal antibody specific for amino acids 376 to 389 of human AIB1 (Transduction Laboratories), horseradish peroxidase-conjugated goat antibodies to mouse immunoglobulin (1:10,000 dilution; Amersham Pharmacia Biotech), and enhanced chemiluminescence reagents (Amersham Pharmacia Biotech).

To determine if the MCF-7 130 kDa species and the in vitro transcription translation product had identical electrophoretic properties, high-resolution electrophoresis was performed on 4% polyacrylamide gels containing Tris-glycine followed by immunoblot analysis. This analysis demonstrated that the mobility of the 130-kDa protein detected in MCF-7 cell extracts was identical to that of the 130-kDa protein produced by in vitro transcription and translation of Δ3-AIB1 cDNA (FIG. 2). This observation suggested that the 130-kDa MCF-7 cell protein was translated from Δ3-AIB1 mRNA present in these cells.

To verify that the Δ3-AIB1 mRNA was translated in vivo, transient transfection of CHO cells (FIG. 2; see FIG. 4a) or COS-1 cells (see FIG. 5a) with the Δ3-AIB1 cDNA was performed. COS-1 and CHO cells were plated at densities of $2\times10^5$ and $5\times10^5$ cells per well, respectively, in six-well plates, and were cultured for 24 h at 37° C. under 5% $CO_2$ in IMEM or Ham's F-12, respectively, supplemented with 5% FBS that had been treated with dextran-coated charcoal. The medium was then replaced with IMEM containing Lipofectamine Plus (Gibco BRL) and expression and reporter plasmids as indicated. After incubation for 3 h, the medium was replaced with IMEM (COS-1 cells) or Ham's F-12 (CHO cells), each containing 5% dextran-coated charcoal-treated FBS and nuclear receptor ligands. Cells were incubated for 24 h and then disrupted in passive lysis buffer (Promega). Portions (20 μl) of the resulting cell extract were assayed for both firefly and renilla luciferase activities with the Dual-Luciferase reporter assay system (Promega).

ME-180 cells were plated at a density of $5\times10^5$ cells per well and cultured for 24 h in IMEM supplemented with 5% dextran-charcoal-treated FBS. They were then incubated for 3 h in IMEM supplemented with Lipofectamine Plus and expression and reporter plasmids. Cells were washed and then incubated in IMEM for an additional 3 h before incubation for 18 h with EGF (5 ng/ml) in serum-free IMEM and subsequent lysis. Because of high background induction of pRL-CMV expression by EGF, firefly luciferase activity was normalized by protein concentration as described previously (32).

Analysis of cell extracts demonstrated that this indeed resulted in the production of a 130-kDa protein, whereas transfection with the full-length AIB1 cDNA yielded only the 156-kDa full-length protein. This latter observation demonstrated that the 130-kDa protein was clearly not the product of proteolytic processing of the full-length protein. Electrophoretic mobility of the 130-kDa protein synthesized in cells transfected with the Δ3-AIB1 cDNA was identical to that of both the 130-kDa AIB1 species present in MCF-7 cell extracts and the product of in vitro transcription-translation of the Δ3-AIB1 cDNA (FIG. 2). Together these data indicated that the endogenous Δ3-AIB1 mRNA present in MCF-7 cells encodes a 130-kDa protein.

Examination of the sequence of Δ3-AIB1 mRNA indicated that the open reading frame of AIB1, which initiates at nt 184 in the full length mRNA would terminate after 90 amino acids in the splice variant (FIG. 1c). This predicted low molecular weight product was not detected in vivo or in vitro. The 130 kDA species was detected by an AIB1 antibody raised against amino acids 376-389 in the amino terminus of the protein. This suggests that the Δ3-AIB1 isoform most likely represents an $NH_2$-terminally truncated form of AIB1 whose synthesis is initiated at an internal translation start site downstream of the splice junction, but prior to amino acid 376. Such internal translational initiation has been described for various mRNAs with extended 5 untranslated regions (34-37). The difference in size between the 156-kDa full-length AIB1 protein and the 130-kDa species suggested that the latter lacks ~210 amino acids of the former, including all of the bHLH region (residues 16 to 88) and most of the PAS A domain (residues 116 to 171) (FIG. 1c). This would place the initiation codon for the 130 kDa protein most likely at the codon at 778 (FIG. 1c). Interestingly, for cells transfected with equivalent amounts of cDNA, the intracellular concentration of Δ3-AIB1 protein was ~10% of that of full-length AIB1 (FIG. 2; see FIG. 4a and FIG. 5a), suggesting that translation initiation of the splice variant was inefficient, possibly because of the long 5' untranslated region of the Δ3-AIB1 mRNA.

Example 3

Δ3-AIB1 mRNA is Over Expressed in Human Breast Cancer

Given that the Δ3-AIB1 splice variant was first detected in a breast cancer cell line, it was next examined whether its expression was restricted to tumor cells. MCF-7 cells are derived from a pleural effusion of metastatic breast cancer, whereas MCF-10A and A1N4 cells are not malignantly transformed and were derived from atypical human breast epithelial hyperplasia (38) and from human mammary epithelial cells treated with benzopyrene (39), respectively.

Figure 3:
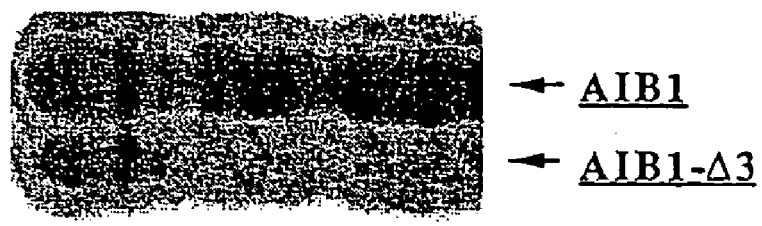
Figure 3:
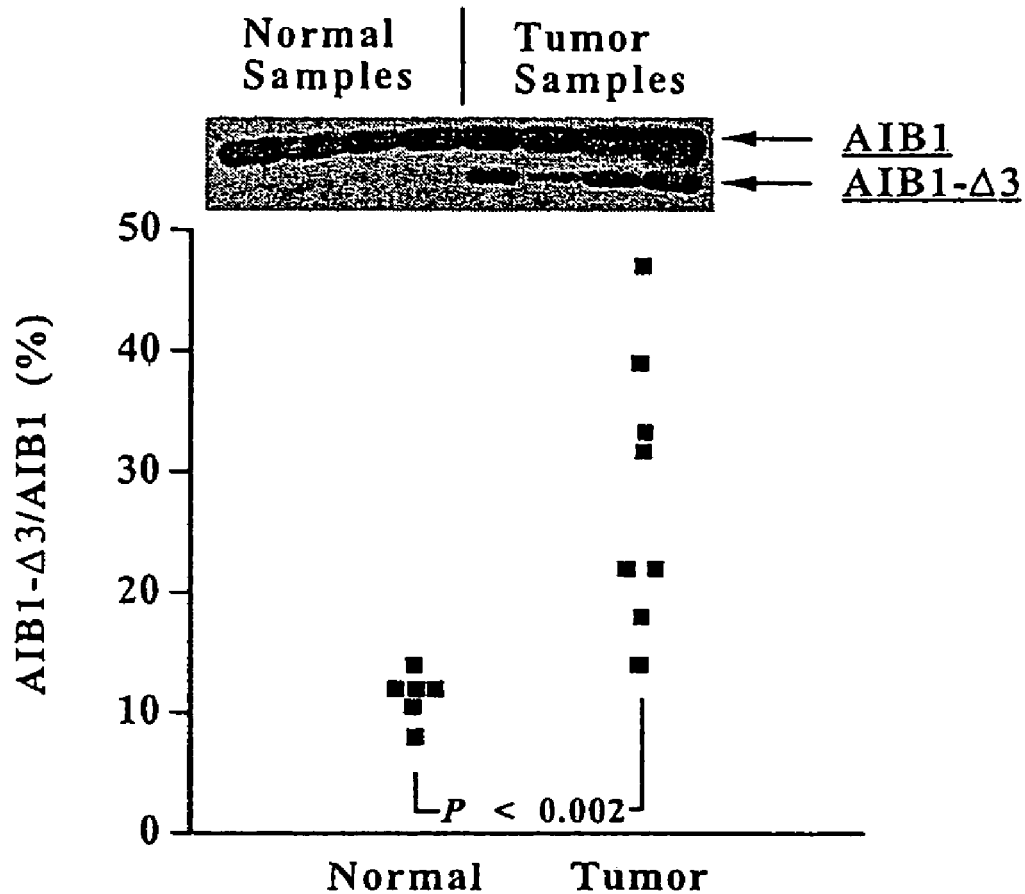

FIG. 3 shows a comparison of the abundance of Δ3-AIB1 mRNA between malignant and nonmalignant human breast tissue and cell lines. FIG. 3(a) shows total RNA isolated from MCF-7, MCF-10A, and A1N4 cells subjected to RT-PCR with primers specific for exons 2 and 5 of AIB1. Reaction products were resolved on a 1% agarose gel and then subjected to Southern blot analysis with a $^{32}$P-labeled oligonucleotide probe specific for exon 4 of AIB1. FIG. 3(b) shows total RNA, isolated from six normal breast and eight breast cancer tissue samples, analyzed as in FIG. 3(a). The amounts of PCR products corresponding to AIB1 and Δ3-AIB1 mRNAs were quantitated by densitometry, and the abundance of the latter was expressed as a percentage of that of the former. The signal of the full-length AIB1 transcript was compared between breast tumors and normal breast tissue with the use of an arbitrary scale; the signals in tumor and normal samples were 1.0±0.46 and 0.7±0.24 (means±SEM), respectively, and they did not differ significantly (P>0.05; Student's t-test). The inset shows a typical blot of 8 of the 14 samples.

RT-PCR followed by Southern blot analysis revealed that the amounts of Δ3-AIB1 mRNA in MCF-10A and AIN4 cells were lower than that of MCF-7 cells (FIG. 3a). By subsequent real-time PCR analysis, using primers specific for AIB1 or its isoform, it was assessed that the ratio of Δ3-AIB1 mRNA/full length AIB1 is 5% in MCF-7 cells, whereas in MCF-10A and AIN4 cells the ratio is 0.5% (data not shown). The abundance of the Δ3-AIB1 mRNA was compared in a series of eight human breast tumors with that in normal tissue obtained from six women undergoing breast reduction mammoplasty. Frozen tissue samples were obtained from the Lombardi Cancer Center Histopathology and Tissue Shared Resource Core. Six normal samples were obtained from individuals undergoing reduction mammoplasty (mean age at time of surgery, 29 years; range, 19 to 54 years); the eight primary breast carcinoma specimens were obtained from women with a mean age at the time of surgery of 51 years (range, 29 to 64 years). The amounts of PCR products corresponding to AIB1 and Δ3-AIB1 mRNAs were quantitated by densitometry, and the abundance of the latter was expressed as a percentage of that of the former. The signal of the full-length AIB1 transcript was compared between breast tumors and normal breast tissue with the use of an arbitrary scale; the signals in tumor and normal samples were 1.0±0.46 and 0.7±0.24 (means±SEM), respectively, and they did not differ significantly (P>0.05; Student's t-test). The inset shows a typical blot of 8 of the 14 samples. The amount of the full-length AIB1 mRNA in tumor samples was slightly greater than that in the normal tissue samples, but this difference was not significant (FIG. 3b). In contrast, the abundance of the Δ3-AIB1 mRNA in the tumor specimens was significantly greater than that in the normal tissue samples, with all but one of the tumors showing an increased amount of this transcript compared with the normal range.

Example 4

Effect of the Δ3-AIB1 Isoform on Nuclear Receptor Function

Figure 4:
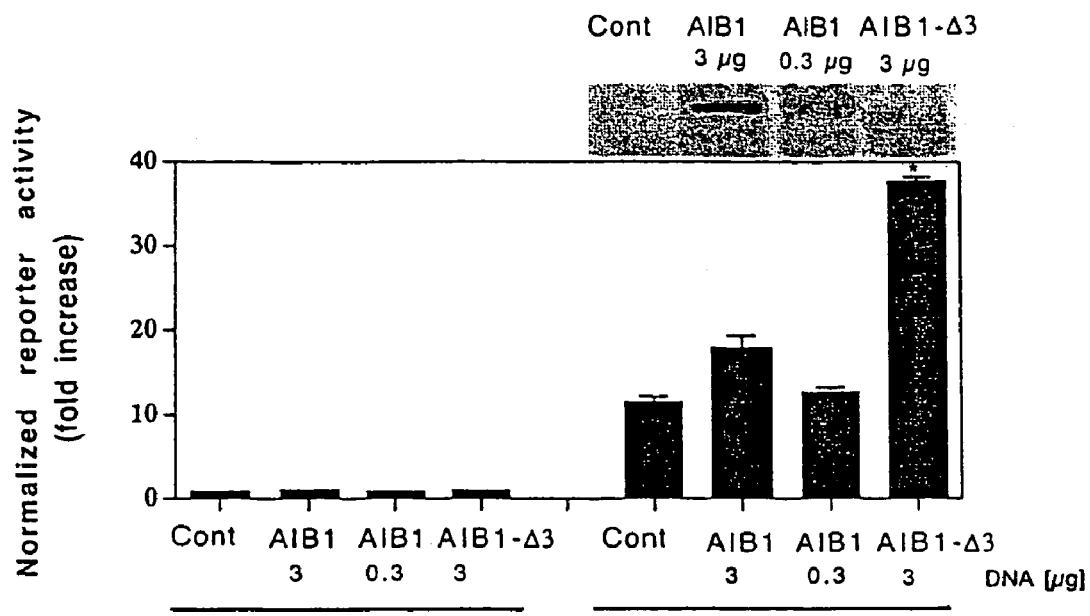
FIG. 4 Effects of AIB1 and Δ3-AIB1 on the activation of estrogen receptor α and progesterone receptor β in CHO cells showing: a cells transfected with either the empty pcDNA3 vector (control), pcDNA3-AIB1, or pcDNA3-AIB1-Δ3, together with an expression vector for human estrogen receptor α, an ERE-luciferase reporter plasmid, and pRL-CMV (inset shows immunoblot analysis of transfected cell lysates probed with antibodies to AIB1); and b cells transfected as in a with the exception that the estrogen receptor vector is replaced with a vector for human progesterone receptor β, and the ERE-luciferase plasmid is replaced with a luciferase reporter construct containing the mouse mammary tumor virus (MMTV) promoter.
Figure 4:
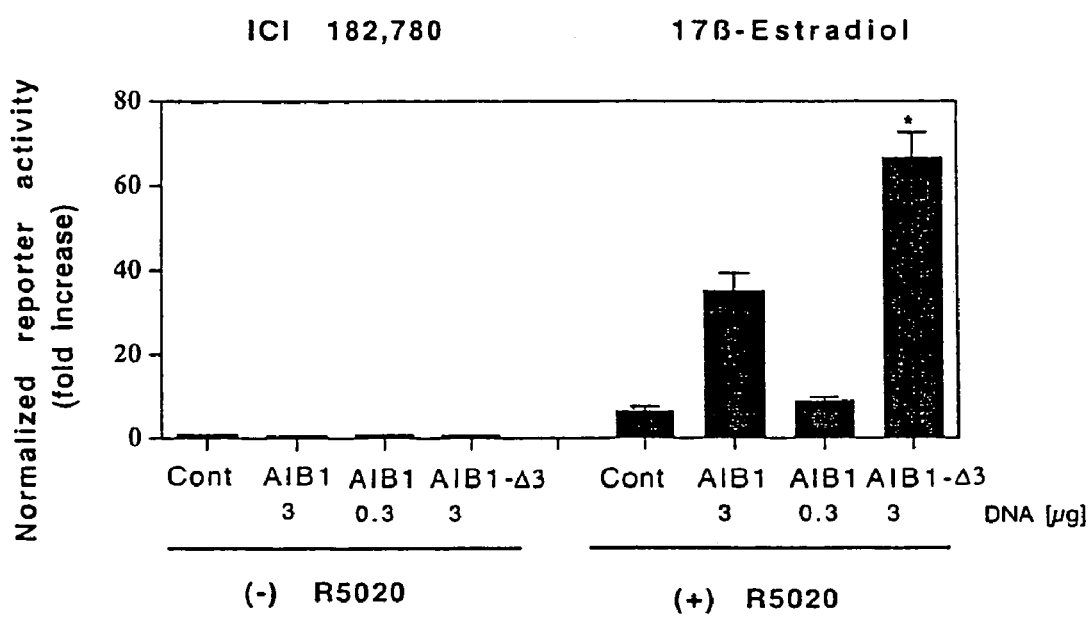

The effect of the deletion of the bHLH and PAS A domains was next examined in Δ3-AIB1 on protein function. AIB1 acts as a coactivator for several nuclear receptors, including those for estrogen and progesterone, which are important in breast carcinogenesis. FIG. 4 shows the effects of AIB1 and Δ3-AIB1 on the activation of estrogen receptor α and progesterone receptor β in CHO cells. In FIG. 4a, cells were transfected with either the empty pcDNA3 vector (3 μg) (control), pcDNA3-AIB 1(0.3 or 3 μg), or pcDNA3-Δ3-AIB1 (3 μg), together with an expression vector for human estrogen receptor α (100 ng), an ERE-luciferase reporter plasmid (1 μg), and pRL-CMV (0.1 ng) (Promega). After incubation for 24 h with either 10 nM estradiol-17β or 100 nM of the estrogen receptor antagonist ICI 182,780, cells were lysed and assayed for luciferase activity. The inset shows immunoblot analysis of transfected cell lysates that were fractionated on 4 to 20% polyacrylamide gradient gels and probed with antibodies to AIB1. FIG. 4b shows cells transfected as in FIG. 4a with the exception that the estrogen receptor vector was replaced with a vector for human progesterone receptor β (20 ng), and the ERE-luciferase plasmid was replaced by a luciferase reporter construct containing the mouse mammary tumor virus (MMTV) promoter (2 μg). Cells were incubated for 24 h in the absence or presence of the progesterone analog R5020 (1 nM) before preparation of lysates for luciferase assay. The firefly luciferase activity of cell lysates was divided by the renilla luciferase activity (internal control), and this ratio (normalized reporter activity) for control cells incubated in the absence of agonist was assigned a value of 1. Data are means±SEM of values from three independent experiments, each performed in triplicate. *P<0.005 versus corresponding value for cells transfected with 3 μg of the AIB1 vector (Student's t test).

Transient Transfection Assays

CHO cells were transfected with expression vectors encoding full-length AIB1 or Δ3-AIB1, an expression vector for estrogen receptor α, and a luciferase reporter plasmid containing an estrogen response element (ERE). Transfection of CHO cells with 3 μg of the AIB1 expression vector resulted in a 1.4-fold increase in estrogen-induced luciferase activity, whereas transfection with 3 μg of the vector for Δ3-AIB1 resulted in a 3.8-fold increase in the estrogen response (FIG. 4a). Given that the abundance of recombinant AIB1 in the transfected cells was about 10 times that of Δ3-AIB1, CHO cells were also transfected with 0.3 μg of the AIB1 vector, which yielded about the same amount of intracellular recombinant protein as did 3 μg of the Δ3-AIB 1 vector (FIG. 4a). Comparison of transfected cells containing approximately equal amounts of recombinant protein thus revealed that AIB1 and Δ3-AIB1 potentiated or enhanced the estrogen response by factors of 1.1 and 3.8, respectively.

Similar transfection experiments were also performed with COS-1 cells and the effects of AIB1 and Δ3-AIB1 on the activation of estrogen receptor a and progesterone receptor β determined. Briefly, cells were transfected and analyzed as in FIG. 4a (the amount of pcDNA3-AIB1 was 3 μg) (FIG. 5a). Cells were transfected with 1 μg of either pcDNA3, pcDNA3-AIB1, or pcDNA-Δ3-AIB1, together with an expression vector for human progesterone receptor β (10 ng), a luciferase reporter plasmid containing the MMTV promoter (1 μg), and pRL-CMV (0.1 ng). After incubation for 24 h in the absence or presence of 0.5 nM R5020, cells were lysed and assayed for luciferase activity (FIG. 5b). Data are means±SEM of values from three independent experiments, each performed in triplicate. *P<0.005 versus the corresponding value for cells transfected with the AIB 1 vector.

Figure 5:
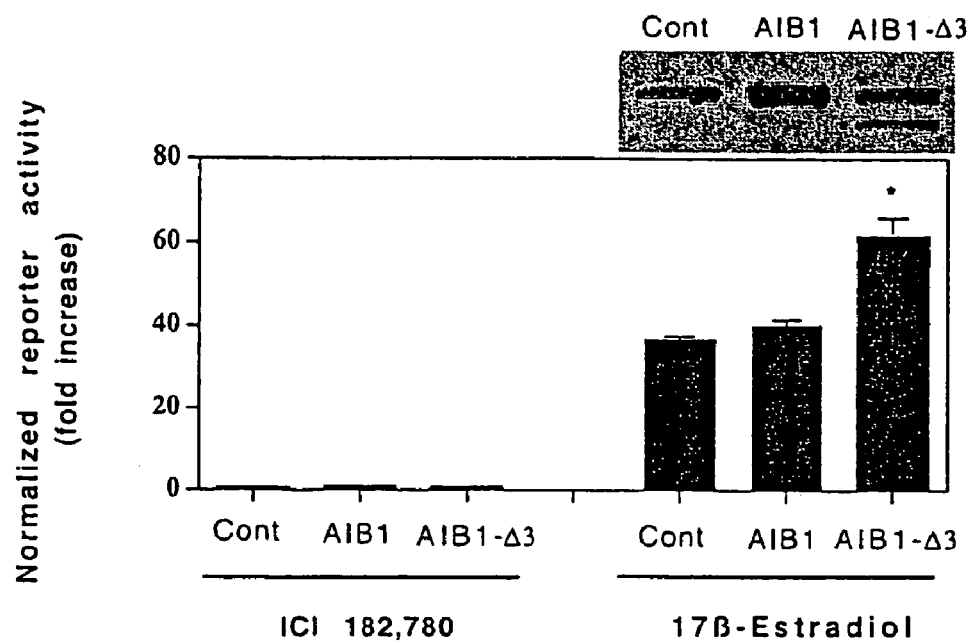
FIG. 5 Effects of AIB1 and Δ3-AIB1 on the activation of estrogen receptor α and progesterone receptor β in COS-1 cells showing: a cells transfected and analyzed as in FIG. 4a; b cells transfected with either pcDNA3, pcDNA3-AIB1, or pcDNA-AIB1-Δ3, together with an expression vector for human progesterone receptor β, luciferase reporter plasmid containing the MMTV promoter and pRL-CMV.
Figure 5:
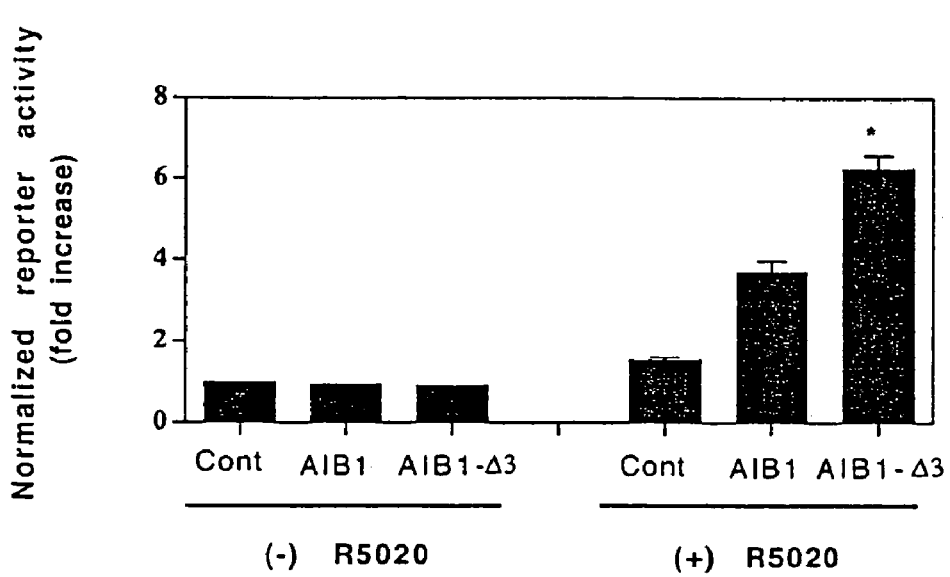

Transfection experiments with COS-1 cells (which express endogenous AIB1) also demonstrated a greater potentiation of the estrogen response by Δ3-AIB1 than by full-length AIB1 (FIG. 5a). The differences between full-length and the Δ3-AIB 1 isoform were seen at different concentrations of estrogen (0.1 to 10 nM) and thus were not due to a change in the affinity of the hormone for its receptor but rather suggests enhanced efficacy of the signaling (data not shown). Similar results were obtained in COS-1 cells with an expression vector encoding progesterone receptor β; the transcriptional response to the progesterone analog R5020 was thus potentiated to a greater extent by Δ3-AIB1 than by AIB1 in both CHO and COS-1 cells (FIG. 4b, FIG. 5b). Of particular note was that small amounts of transfected Δ3-AIB1 protein had significant effects on ER and PR induced transcription even against a relatively high background of full-length AIB1 (FIG. 5).

Example 5

Effect of the Δ3-AIB1 Isoform on EGF Signaling

The fact that members of the p160 SRC family act as coactivators in intracellular signaling pathways that activate transcription factors other than nuclear receptors (30,31) prompted an examination of whether Δ3-AIB1 might be able to sensitize breast cancer cells to growth factor signaling. Overexpression of members of the families of epidermal growth factor (EGF) ligands or EGF receptors is important in the malignant progression of breast cancer (40). Such growth factors also contribute to the hormone-independent phenotype of breast tumors and the HER-2 receptor is a target of current therapies (41). To determine whether AIB1 and Δ3-AIB1 affect EGF signaling, ME-180 human squamous cell carcinoma cells were transfected with the respective expression vectors and with a luciferase reporter plasmid containing the promoter of the fibroblast growth factor-binding protein (FGF-BP) gene. FGF-BP functions as an angiogenic switch molecule (42) that is overexpressed in breast cancer, and whose gene is activated by EGF in squamous cell and breast cancer cell lines (32).

Figure 6:
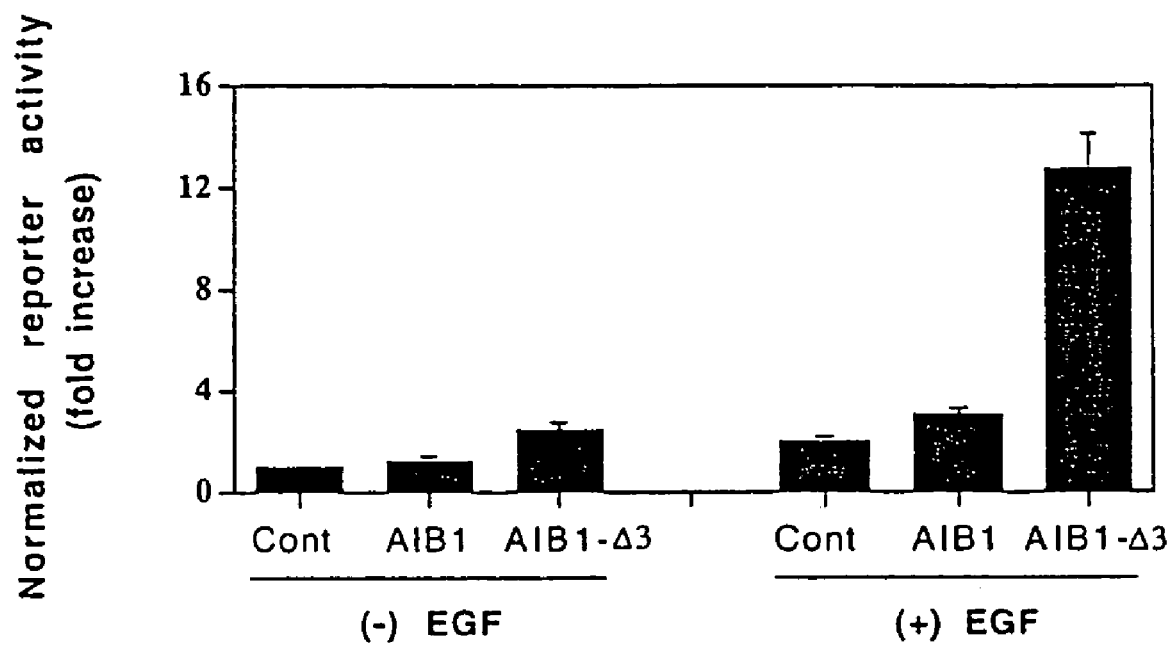
FIG. 6 Effects of AIB1 and AIB1-Δ3 on activation of the FGF-BP gene promoter by EGF in ME-180 cells.

Cells were transfected with 3 μg of either pcDNA3, pcDNA3-AIB1, or pcDNA3-AIB1-Δ3, together with a luciferase reporter plasmid containing the human FGF-BP gene promoter (1 μg) (32) (FIG. 6). After incubation of cells for 18 h in the absence or presence of EGF (5 ng/ml) in serum-free medium, cell extracts were prepared and assayed for luciferase activity. Activity was normalized by protein concentration, and the normalized activity values were then expressed relative to that of cells transfected with pcDNA3 and not exposed to EGF. Data are means±SEM of values from three independent experiments, each performed in triplicate. *$P<0.01$ versus the corresponding value for control cells.

As reported previously EGF induced a 2.5-fold increase in reporter activity in control cells transfected with the empty expression vector (FIG. 6). The basal EGF induction was increased slightly by transfection of the full length AIB1 expression vector whereas EGF induction was increased approximately 6-fold by expressing recombinant AIB 1-Δ3.

Example 6

In Vivo Targeting of Nuclear Receptor Coactivator AIB1 with siRNA

In this example, it was determined whether selective reduction of the gene expression of a nuclear receptor coactivator AIB1 or its more active isoform ?3-AIB1 leads to an inhibition of the growth of human breast cancer cells in cell culture and of xenograft tumors in mice.

Inhibition of Proliferation of Cells in Culture

Figure 7:
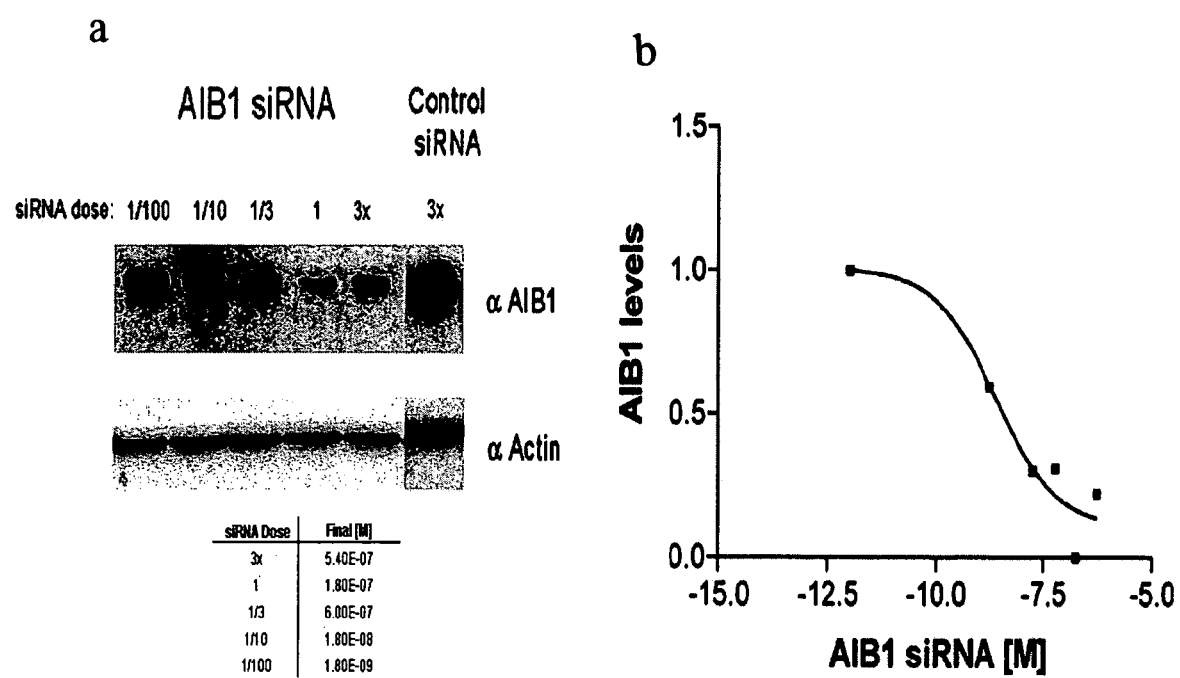
FIG. 7. AIB1 siRNA decreases endogenous AIB1 protein levels in a dose dependent manner a Histogram of siRNA dose verses mRNA levels; and b cell number±growth factor was determined with AIB1 up or down and is expressed relative to control.

MCF-7 cells were transiently transfected with varying concentrations (log M is given) of either siRNA targeted against AIB1 mRNA or scrambled, nonspecific siRNA (control) (FIG. 7). After 72 hrs, whole cell extracts were harvested and probed with a monoclonal antibody to AIB1. The membrane was stripped and reprobed for actin as a loading control. Bands were quantitated by densitometry. Percent AIB1 levels were calculated by taking the ratio of AIB1 levels in the control siRNA versus AIB1 siRNA transfected cells. An IC50 of 0.2 μM and an effect size of 90% were estimated from the concentration-response (FIG. 7, right panel).

Figure 8:
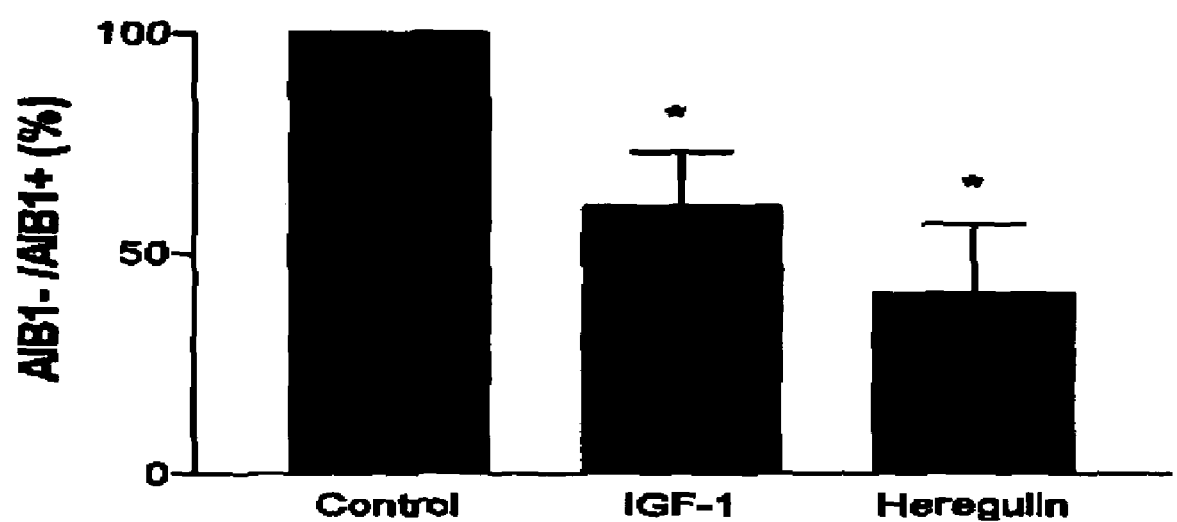
FIG. 8 Growth factor dependent proliferation of MCF-7 cells is reduced by a tetracycline-regulated AIB1 targeted ribozyme.

In addition, growth factor dependent proliferation of MCF-7 cells is reduced by a tetracycline-regulated AIB1 targeted ribozyme (FIG. 8). AIB1 siRNA decreases endogenous AIB1 protein levels in a dose-dependent manner. siRNA dose verses mRNA levels and cell number±growth factor were determined with AIB1 up or down and is expressed relative to control. Thus, using a regulatable AIB1-directed ribozyme, it was found that down regulation of endogenous AIB1 levels in MCF-7 breast cancer cells results in the loss of estrogen-sensitive growth. This is mainly through reduction in estrogen-dependent inhibition of apoptosis.

Figure 9:
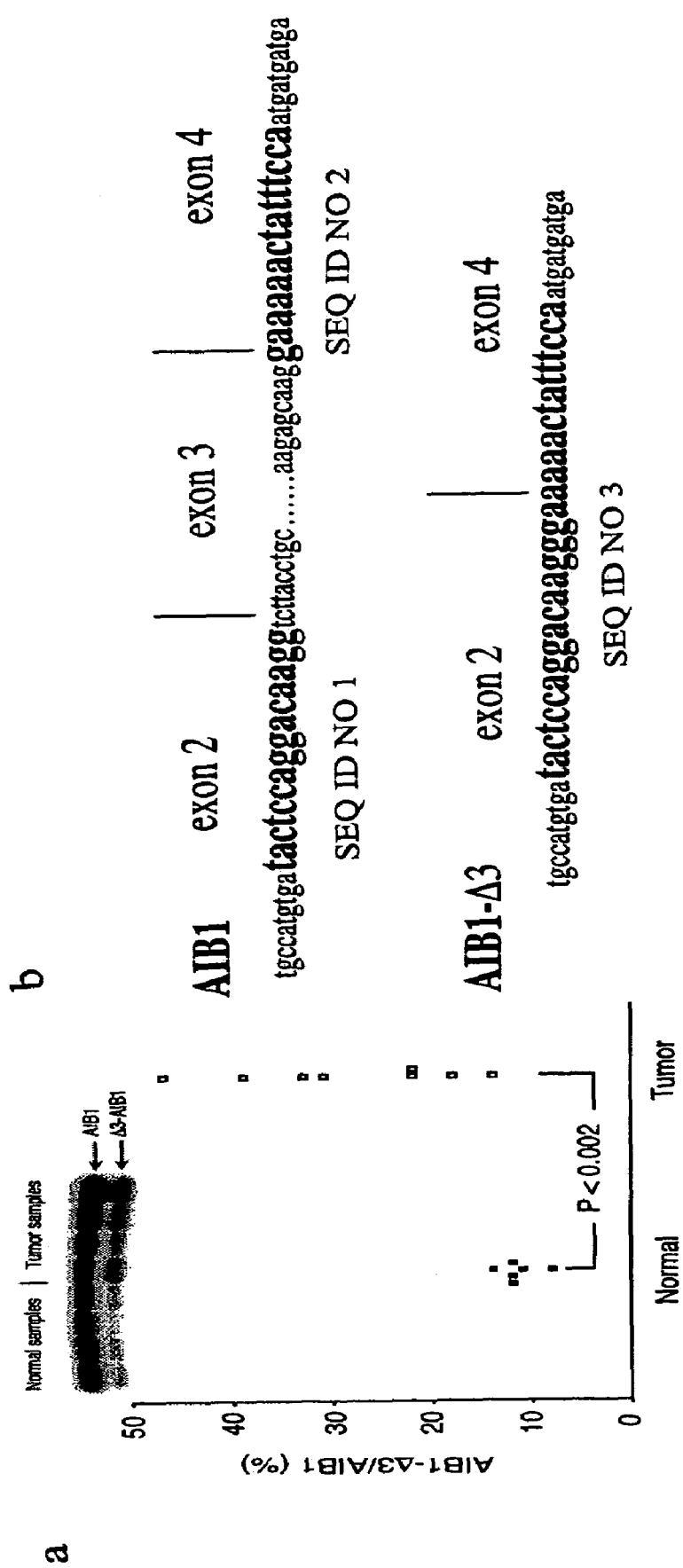
FIG. 9 a RT-PCR for AIB1 and Δ3-AIB1 RNA from normal and breast cancer tissue wherein the signal between breast and normal tissue was compared using an arbitrary scale; and b sequence of exon junctions for AIB1 and Δ3-AIB1 isoform (SEQ ID NOS 1-3, respectively in order of appearance.

Thus, by designing siRNA molecules to target AIB1 or Δ3-AIB1, cellular levels of AIB1 can be reduced. The IC50 for this effect is 0.2 mM which indicates that it is possible to achieve tissue levels of siRNA for a therapeutic effect in vivo with only a few mg of siRNA per dose. The 5' region of the AIB1 mRNA was chosen as the initial target because it bears no homology to other mRNA sequences as determined by a Blast search of the entire human genome. After a single liposome transfection into MCF-7 breast cancer cells this siRNA produced an up to 90% reduction in AIB1 protein levels as measured by Western blot analysis (FIG. 9). This effect was maintained for up to 72 hrs after addition of siRNA to the cells for a time period of 4 hours. Under this objective, alternative regions of AIB1 mRNA are targeted and tested to produce reductions in AIB1 gene expression at a lower IC50. To narrow down the chosen regions, areas common to Src-1 and Src-2 are excluded from this analysis as are common domain sequences such as the histone acetyl transferase domain and PAS/HLH sequence domains of known proteins. The remaining areas are used as candidates for a detailed Blast search. The best ten sequences are selected to make siRNA molecules. To specifically target Δ3-AIB1, the junction of exons 2 to 4 is targeted which is a fusion that unique to this isoform (FIG. 9). A series of siRNA molecules between −13 and +13 relative to the junction (−9/+13, −10/+12, +11/+11, −12/+10, −13/+9 etc.) are synthesized and their effect on target Δ3-AIB1 relative to full-length AIB1 determined (FIG. 9b). Residual levels of both AIB1 isoforms are measured by Western blotting after electrophoretic separation of the isoforms on 4% polyacrylamide gels as described previously. Each siRNA molecule is tested at 5 concentrations of 1, 0.3, 0.1, 0.03 and 0.01 mM to determine the maximum reduction and the IC50. MCF-7 cells are the initial cell line used and confirmatory experiments are also run in T47D and MDA MB231 human breast cancer cells. These cells lines are chosen because they represent excellent model systems for human breast cancer: MCF-7 cells are responsive to estrogens, harbor the 20 q AIB1 amplicon and express high levels of AIB1/Δ3-AIB1 (14). T47D cells contain higher levels of AIB1 and Δ3-AIB1 than normal mammary epithelium yet several fold lower levels than MCF-7 cells (14). They do not harbor the 20 q amplicon, are estrogen responsive and, at least with respect to AIB1 expression levels, mimic a large portion of clinical breast cancers. MDA MB231 cells are chosen because they respond to growth factors for proliferation, are hormone-independent (ER-negative) and are a highly tumorigenic and metastatic in animal models. MDA MB231 cells are relatively invasive and have been well characterized in terms of both in vitro and in vivo invasive and chemotactic characteristics. This cell line responds to EGF and IGF with increased chemotaxis and to HGF with increased invasive capacity (49, 50). This cell line expresses intermediate levels of AIB1. Typically, the Prizm/Graphpad program is used for curve fittings. For a 5-point siRNA dose response curve plus a negative control in triplicate, the cellular levels of AIB1 isoforms can easily be quantitated using serial Western blots as shown in FIG. 7. Once the concentration that achieves approximately 80% efficacy has been established for each siRNA molecule, the duration of the effect of each molecule can be examined at that concentration. Potency and thus, the drug concentration needed for the targeted effect level, can be tested empirically and those siRNAs chosen for use in animals that show the best dose/time/response (lowest dose to get a 3 day effect >50%). In the experiment described in FIG. 7, it was found that the effects of the siRNA directed at AIB1 were preserved for at least 72 hours. Some reports have claimed that siRNA effects can be prolonged to >100 hours in vitro after a single administration (51). Therefore, time course experiments are run for up to 120 hours with the optimal dose of each siRNA to determine the duration of the RNA silencing and whether this differs amongst the siRNAs chosen.

To determine if siRNA-induced reduction of cellular levels of AIB1 or Δ3-AIB1 can change the phenotype of breast cancer, cell lines are tested to examine if siRNA-mediated depletion of AIB1 or Δ3-AIB1 result in estrogen or growth factor-induced changes in cellular proliferation and soft agar colony formation. It is first determined if there are changes in doubling time or in colony formation under anchorage-independent growth conditions in soft agar. In addition to spontaneous growth, cells are cultured in serum only or EGF (10 to 100 ng/ml), IGF-1 (10 to 100 ng/ml), heregulin (10 to 100 ng/ml), HGF (hepatocyte growth factor; 10 to 100 ng/ml). The growth responses after 2, 4, 6 and 8 days are compared in the presence or absence of siRNA (+/− growth factor) at the optimal concentration of siRNA previously determined. For the growth assays, it is only necessary to test the siRNA molecules that have had effective and long lasting effects as well as those that are specific for Δ3-AIB1. A single addition of siRNA is used initially and several dosings of siRNA (every other day) for those conditions that showed effects only after the initial dosing. For the soft agar assays, cells are cultured in the presence or absence of EGF, IGF-1, heregulin, HGF or serum (concentrations as above) with or without siRNA (only one dose is used initially). After at least 7 days of incubation, colonies are counted with an image analyzer. In addition, experiments with the MCF-7 and T47D cells can include estrogen to determine whether AIB1 contributes to synergism between growth factor and estrogen-mediated signaling.

Cell cycle/apoptosis. Since growth factors contribute to cell cycle progression as well as inhibition of apoptosis in human breast cancer cells, whether any siRNA-induced effects on cell growth can be analyzed. This might have resulted from a reduced ability of the cells to progress through the cell cycle or whether this effect is based on their altered susceptibility towards apoptosis. A similar analysis with estrogen-induced cell growth was performed which found that AIB1 was predominantly acting through inhibition of apoptosis rather than through changes in cell cycle progression (29). However, AIB1 has been demonstrated to be important for the expression of cell cycle genes (52) and AIB1 modulation of cell-cycle progression is more important for growth factor signaling than for hormone signaling. Cell cycle analysis is performed by FACS analysis and apoptosis is measured with propidium iodide-annexinV-FITC dual staining and FACS analysis. Both approaches have been described (29).

These experiments provide a comprehensive view of the impact of AIB1 reductions induced by siRNA on gross phenotypic changes regulated by growth factors and/or hormones. For specificity controls, it can be determined if other related genes such as Src-1 are unaffected by the treatment control. In addition, mutated siRNA which has several bases changed can be used to determine specificity.

Inhibition of Growth of Xenograft Tumors in Mice

The deletion of the AIB1 (CIP) gene in mice resulted in a surprising phenotype where mice had reduced overall growth due, in part, to reduced serum IGF levels (53, 54), but mainly because IGF signaling was reduced in AIB1$^{-/-}$ cells (53). Serum induction of proliferation in AIB1$^{-/-}$ cells was unaltered (53). In human breast cancer cells it was found that the isoform Δ3-AIB1 can strongly potentiate EGF signaling (48) and similar to the AIB1 knock-out in mice. The reduction of overall AIB1 levels in MCF-7 cells inhibits IGF-1 and heregulin induced growth, but does not affect growth under control conditions, i.e. in the presence of serum (FIG. 8). Thus, for the targeting of AIB1, siRNA against isoforms of AIB1 is a viable therapy for the treatment of human breast cancer.

These observations indicate that a central role of AIB1 in a defined number of signaling pathways induced by growth factors that are known to play pivotal roles in the malignant progression of breast cancer. Over expression of growth factor receptors (HER-2/neu and EGFR) are correlated with a more aggressive phenotype and with a decreased responsiveness to antiestrogen therapy. Thus, over expressed AIB1 and, in particular, the isoform Δ3-AIB1 is a master regulator that drives a more aggressive phenotype of breast cancer and AIB1 and Δ3-AIB1 can be used as therapeutic targets in breast cancer. The validity of AIB 1 as a therapeutic target is based on the facts that: (i) AIB1 is a rate-limiting regulator for estrogen and growth factor signaling in breast cancer; (ii) AIB1 is over expressed selectively in breast cancer cells and not in non-transformed tissues; (iii) the knock-out of the AIB1 gene in mice indicates that the side-effects of AIB1 reduction are limited to the growth phase of the body before adulthood and to the reproductive system indicating that that in an adult, target-specific side effects are very likely small; (iv) selective reduction of the Δ3-AIB1 isoform is possible by generating siRNAs that target the splice junction of exons 2/4 (see FIG. 9b) and, thus, only deplete this isoform. Accordingly, targeting Δ3-AIB1 isoform is more effective against cancer than targeting full-length AIB1. As shown in FIG. 1a, the Δ3-AIB1 isoform is selectively over expressed in breast cancer cells and cancer tissues from patients and is barely detectable in normal breast tissues. In addition, this isoform is significantly more potent than full-length AIB1 on a molar basis and thus contributes to a large percentage of AIB1 effects on growth and proliferation in cancerous tissue; and (v) because AIB1 is selectively over expressed in tumor tissues, the side effects from therapeutic targeting of the Δ3-AIB1 isoform are expected to be minimal.

The use of short, double-stranded RNA molecules that cause RNA interference (RNAi) have proven to be an effective and selective method of reducing cellular mRNA (51, 55, 56, 57, 58). A short, double-stranded RNA (dsRNA) is synthesized to generate small interfering, siRNA that matches a sequence in the target gene. Upon introduction to cells, the endogenous cellular enzymatic degradation system triggers degradation of the mRNA that matches its sequence via the siRNA/mRNA complex. If the siRNA is short (21-23 mer), the double-stranded RNA apparently evades cell defense mechanism to long double-stranded RNA of viral origin, which normally provokes a total shut down in cellular protein synthesis. The advantage of using siRNA molecules is that they are short and stable, easily synthesized and are able to degrade cellular RNA at very low concentrations, much lower than that amount used with antisense oligonucleotides or ribozymes (51, 55, 56, 57, 58). In addition, siRNA can produce a prolonged down regulation of mRNA in cells in culture. The respective data for AIB1 targeting are shown in FIG. 3. A 90% reduction of AIB1 protein in MCF-7 human breast cancer cells with an IC50 of approximately 0.2 mM was observed after a single addition of siRNA and this reduction is sustained for at least 72 hrs. Thus, in hand is an siRNA species that can target AIB1 effectively in cells in culture. It is next determined if it is possible to selectively target AIB1 and its isoform in vivo and, thus, if this prevents breast cancer development and proliferation.

Therapeutic Administration of siRNA Directed Against AIB1

Utilizing the most potent of the AIB1 and Δ3-AIB1 siRNAs identified, one can determine a regimen of administration of siRNA to animals to produce a sustained reduction of AIB1 in animal tumors and ultimately an anti-tumorigenic effect in vivo. Distribution and approximate tissue concentration is determined after siRNA administration. From this, an optimal dose and dosing interval is assessed for the animal. Fluorescently tagged (FITC) active siRNA molecules are prepared and injected ip or iv into nude mice that carry at least one MCF-7 xenograft tumor each. The tissue levels of siRNA are estimated in the tumor, liver, muscle, kidney and brain at several time points after injection. From cell culture studies, it was shown that tissue concentrations of 0.1 to 0.3 micromolar can reduce AIB1 protein significantly (see FIG. 7). To achieve this concentration in vivo, one would need to inject approximately 2 to 6 mg of siRNA i.p. per mouse. To maintain these levels will depend on the half life of the siRNA liposome complex in vivo and this is determined using fluorescein conjugated molecules. Animals are sacrificed at 6, 12, 24, 48 and 72 hours of i.p. injection of the tagged siRNA and the levels of fluorescein conjugated molecule determined by fluorescence detection in the homogenates of liver, kidney, muscle, brain and tumor. FITC labeled siRNA is imaged after treatment of MCF-7 cells in vitro. In parallel with the measurement of siRNA levels by fluorescence, AIB1 levels are measured in the tumors by Western blot. Thus, the time course of drug concentrations is compared with the time-effect relationship. After analysis of the first series with a single intraperitoneal dose, the dose interval (bid, tid etc.) and/or dose level or even the route of administration (intratumoral, i.v.) can be modulated if that promised better efficacy based on AIB1 levels. To study efficacy of siRNA not only on the target gene, but on tumor growth, MBA-MB-231, MCF-7 or T47D cells are implanted into mammary glands of athymic nude mice and their growth followed. In the first series of experiments, systemic administration of siRNA, most likely twice per week i.p., initiates after the formation of palpable tumors. Five mice/group and two tumor inoculum sites per mouse comprise one treatment or one control arm. One can start with two to three i.p. doses of siRNA per week, but this would be modified to more frequent (daily) or less frequent (weekly) dosing as time course studies require. Dosing is continued for the whole duration of the experiment. Tumor growth is monitored for up to two months following implantation and tumor size estimated from the product of perpendicular diameters of the tumor (twice weekly). Tumors are stained for proliferation (by PCNA staining) and mitotic cells, apoptosis (TUNEL staining) and the number of blood vessels. Statistical considerations and evaluations are well known. Targeting AIB1 by regulatable ribozymes in MCF-7 xenograft tumors will not only delay tumor growth, but will induce complete regression of implanted tumors due to siRNA. Treatment with siRNA would be stopped after tumor regression and patients is followed to monitor for possible tumor re-growth. The effect of siRNA is tested on large established tumors of approximately 1 cm in their largest diameter. The extent to which apoptosis may be induced can be assayed by harvesting and staining of the tumor tissues after 2 to 3 weeks of siRNA treatment.

Other embodiments and uses of the invention will be apparent to those skilled in the art from consideration of the specification and practice of the invention disclosed herein. All references cited herein, including all publications, all U.S. and foreign patents and patent applications, and U.S. Provisional Application No. 60/302,648 (i.e. the priority document), are specifically and entirely incorporated herein by reference. It is intended that the specification and examples be considered exemplary only, with the true scope and spirit of the invention indicated by the following claims.

REFERENCES

1. Blanco, J. C., Wang, I. M., Tsai, S. Y., Tsai, M. J., O'Malley, B. W., Jurkuta, P. W., Haussler, M. R., and Ozato, K. (1995) *Proc Natl Acad Sci USA* 92, 1535-1539.
2. Ing, N. H., Beekman, J. M., Tsai, S. Y., Tsai, M. J., and O'Malley, B. W. (1992) *J Biol Chem* 267, 17617-17623.
3. McEwan, I. J., and Gustafsson, J. A. (1997) *Proc. Natl. Acad. Sci. USA* 94, 8485-8490.
4. Rochette-Egly, C., Adam, S., Rossignol, M., Egly, J.-M., and Chambon, P. (1997) *Cell*, 97-107.
5. Sadovsky, Y., Webb, P., Lopez, G., Baxter, J. D., Fitzpatrick, P. M., Ginzang-Ginsberg, E., Cavailles, V., Parker, M. G., and Kushner, P. J. (1995) *Mol Cell Biol* 15, 1554-1563.
6. Schulman, I. G., Chakravati, D., Juguilon, H., Romo, A., and Evans, R. M. (1995) *Proc Natl Acad Sci USA* 92, 8288-8292.
7. Halachmi, S., Marden, E., Martin, G., MacKay, H., Abbondanza, C., and Brown, M. (1994) *Science* 264, 1455-1458.
8. Cavailles, V., Dauvois, S., L'Horset, F., Lopez, G., Hoare, S., Kushner, P. J., and Parker, M. G. (1995) *EMBO J* 14, 3741-3751.
9. Onate, S. A., Tsai, S. Y., Tsai, M.-J., and O'Malley, B. W. (1995) *Science* 270, 1354-1357.
10. Voegel, J. J., Heine, M. J. S., Zechel, C., Chambon, P., and Gronmeyer, H. (1996) *EMBO J* 15, 3667-3675.
11. Hong, H., Kohli, K., Trivedi, A., Johnson, D. L., and Stallcup, M. R. (1996) *Proc. Natl. Acad. Sci.* 93, 4948-4952.
12. Glass, C. K., Rose, D. P., and Rosenfeld, M. G. (1997) *Curr. Opin. Cell Biol.* 9, 222-232.
13. McKenna, N. J., Lanz, R. B., and O'Malley, B. W. (1999) *Endocrine Reviews* 20, 321-344.
14. Anzick, A. L., Kononen, J., Walker, R. L., Azorsa, D. O., Tanner, M. M., Guan, X.-Y., Sauter, G., Kallioniemi, O.-P., Trent, J. M., and Meltzer, P. S. (1997) *Science* 277, 965-968.
15. Chen, H., Lin, R. J., Schiltz, R. L., Chakravarti, D., Nash, A., Nagy, L., Privalsky, M. L., Nakatani, Y., and Evans, R. M. (1997) *Cell* 90, 569-580.
16. Suen, C.-S., Berrodin, T. J., Mastroeni, R., Cheskis, B. J., Lyttle, C. R., and Frail, D. E. (1998) *J Biol Chem* 273, 27645-27653.
17. Li, H., Gomes, P. J., and Chen, J. D. (1997) *Proc. Natl. Acad. Sci. USA* 94, 8479-8484.

18. Takeshita, A., Cardona, G. R., Koibuchi, N., Suen, C.-S., and Chin, W. W. (1997) *J Biol. Chem.* 272, 27629-27634.
19. Yeh, S., Miyamoto, H., Shima, H., and Chang, C. (1998) *Proc Natl Acad Sci USA* 95, 5527-5532.
20. Kamei, Y., Xu, L., Heinzel, T., Torchia, J., Kurokawa, R., Gloss, B., Lin, S. C., Heyman, R. A., Rose, D. W., Glass, C. K., and Rosenfeld, M. G. (1996) *Cell* 85, 403-414.
21. Yang, X.-Y., Ogryzko, V. V., Nishikawa, J.-I., Howard, B. H., and Nakatani, Y. (1996) *Nature* 382, 319-324.
22. Ogryzko, V. V., Schlitz, R. L., Russanova, V., Howard, B. H., and Nakatani, Y. (1996) *Cell* 87, 953-959.
23. Bannister, A. J., and Kouzarides, T. (1996) *Nature* 382, 319-324.
24. Spencer, T. E., Jenster, G., Burcin, M. M., Allis, D. C., Zhou, J., Mizzen, C. A., McKenna, N. J., Onate, S., Tsai, S. Y., Tsai, M.-J., and O'Malley, B. W. (1997) *Nature* 389, 194-198.
25. Guan, X.-Y., Xu, J., Anzick, S. L., Zhang, H., Trent, J. M., and Meltzer, P. S. (1996) *Cancer Research* 56, 3446-3450.
26. Bautista, S., Valles, H., Walker, S. L., Anzick, S., Zellinger, R., Meltzer, P., and Theillet, C. (1998) *Clin. Cancer Res.* 4, 2925-2929.
27. List, H.-J., Reiter, R., Singh, B., Wellstein, A., and Riegel, A. T. (2001) *Breast Cancer Res and Treatment*, 68:21-8.
28. Tikkanen, M. K., Carter, D. J., Harris, A. M., Le, H. M., Azorsa, D. O., Meltzer, P. S., and Murdoch, F. E. (2000) *Proc Natl Acad Sci USA* 97(23), 12536-40.
29. List, H. J., Lauritsen, K. J., Reiter, R., Powers, C., Wellstein, A., and Riegel, A. T. (2001) *J Biol Chem* 276:23763-8.
30. Belandia, B., and Parker, M. G. (2000) *J Biol Chem*, 275, 30801-30805.
31. Lee, S. K., Kim, H. J., Kim, J. W., and Lee, J. W. (1999) *Mol Endocrinol* 13(11), 1924-33.
32. Harris, V. K., Coticchia, C. M., Kagan, B. L., Ahmad, S., Wellstein, A., and Riegel, A. T. (2000) *J. Biol. Chem.* 275, 10802-10811.
33. Fang, W. J., Hartmann, N., Chow, D., Riegel, A. T., and Wellstein, A. (1992) *J Biol. Chem.* 267, 25889-25897.
34. Nanbru, C., Lafon, I., Audigier, S., Gensac, M. C., Vagner, S., Huez, G., and Prats, A. C. (1997) *J Biol Chem* 272(51), 32061-6.
35. Stoneley, M., Paulin, F. E., Le Quesne, J. P., Chappell, S. A., and Willis, A. E. (1998) *Oncogene* 16(3), 423-8.
36. Akiri, G., Nahari, D., Finkelstein, Y., Le, S. Y., Elroy-Stein, O., and Levi, B. Z. (1998) *Oncogene* 17(2), 227-36.
37. Vagner, S., Gensac, M. C., Maret, A., Bayard, F., Amalric, F., Prats, H., and Prats, A. C. (1995) *Mol Cell Biol* 15(1), 35-44.
38. Soule, H. D., Maloney, T. M., Wolman, S. R., Peterson, W. D., Jr., Brenz, R., McGrath, C. M., Russo, J., Pauley, R. J., Jones, R. F., and Brooks, S. C. (1990) *Cancer Res* 50(18), 6075-86.
39. Stampfer, M. R., and Bartley, J. C. (1985) *Proc Natl Acad Sci USA* 82(8), 2394-8.
40. Dickson, R. B., and Lippman, M. E. (1995) *Endocrine Reviews* 16, 559-589.
41. Slamon, D. J., Leyland-Jones, B., Shak, S., Fuchs, H., Paton, V., Bajamonde, A., Fleming, T., Eiermann, W., Wolter, J., Pegram, M., Baselga, J., and Norton, L. (2001) *N Engl J Med* 344(11), 783-92.
42. Czubayko, F., Liaudet-Coopman, E. D. E., Aigner, A., Tuveson, A. T., Berchem, G., and Wellstein, A. (1997) *Nature Med.* 3, 1137-1140.
43. Wu, X., Li, H., and Chen, J. D. (2001) *J Biol Chem* 28, 28.
44. Goldman, P. S., Tran, V. K., and Goodman, R. H. (1997) *Recent Prog Horm Res* 52, 103-19.
45. Kushner, P. J., Agard, D. A., Greene, G. L., Scanlan, T. S., Shiau, A. K., Uht, R. M., and Webb, P. (2000) *J Steroid Biochem Mol Biol* 74(5), 311-7.
46. Kurebayashi, J., Otsuki, T., Kunisue, H., Tanaka, K., Yamamoto, S., and Sonoo, H. (2000) *Clin Cancer Res* 6(2), 512-8.
47. Bouras, T., Southey, M. C., and Venter, D. J. (2001) *Cancer Res* 61(3), 903-7.
48. Reiter, R., A. Wellstein and A. T. Riegel (2001) J. Biol. Chem. 276, 39736-41.
49. Price, J. T., T. Tiganis, A. Agarwal, D. Djakiew, and E. W. Thompson 1999. Cancer Res. 59:5475-8.
50. Trusolino, L., S. Cavassa, P. Angelini, M. Ando, A. Bertotti, P. M. Comoglio, and C. Boccaccio 2000. Faseb J. 14:1629-40.
51. Elbashir, S. M., W. Lendeckel, and T. Tuschl 2001. Genes Dev. 15:188-200.
52. Planas-Silva, M. D., Y. Shang, J. L. Donaher, M. Brown, and R. A. Weinberg 2001. Cancer Res. 61:3858-62.
53. Wang, Z., D. W. Rose, O. Hermanson, F. Liu, T. Herman, W. Wu, D. Szeto, A. Gleiberman, A. Krones, K. Pratt, R. Rosenfeld, C. K. Glass, and M. G. Rosenfeld 2000. Proc Natl Acad Sci USA. 97:13549-13554.
54. Xu, J., L. Liao, G. Ning, H. Yoshida-Komiya, C. Deng, and B. W. O'Malley 2000. Proc Natl Acad Sci USA. 97:6379-84.
55. Bass, B. L. 2001. RNA interference. Nature. 411:428-9.
56. Bosher, J. M., and M. Labouesse 2000. Nat Cell Biol. 2:E31-6.
57. Caplen, N. J., S. Parrish, F. Imani, A. Fire, and R. A. Morgan 2001. Proc Natl Acad Sci USA. 98:9742-7.
58. Carthew, R. W. 2001. Curr Opin Cell Biol. 13:244-8.
59. Fire, A, S. Xu, M. K. Montgomery, S. A. Kostas, S. E. Drivers and C. C. Mello, 1998. Nature 391:806-811.
60. Wianny, F and M. Zemicka-Goetz, 2000 (Feb). Nature Cell Biol. 2:70-75.
61. Brummelkamp, R. Bernards, and R. Agami, 2002. Science 296:550-553.
62. G. Storz, 2002. Science 296:1260-1263.
63. R. H. A. Plasterk, 2002. Science 296:1263-1265.
64. P. D. Zamore, 2002. Science 296:1265-1269.
65. P. Ahlquist, 2002. Science 296:1270-1273.

The invention claimed is:

1. An isolated nucleic acid sequence that encodes a steroid receptor coactivator Amplified In Breast (AIB1) protein isoform, wherein the isoform is Δ3-AIB1, and said nucleic acid comprises SEQ ID NO:3.

2. A vector that contains the nucleic acid of claim 1.

3. An isolated recombinant cell that contains the nucleic acid of claim 1.

* * * * *